(12) United States Patent
Chojnowski et al.

(10) Patent No.: US 10,813,715 B1
(45) Date of Patent: Oct. 27, 2020

(54) SINGLE IMAGE MOBILE DEVICE HUMAN BODY SCANNING AND 3D MODEL CREATION AND ANALYSIS

(71) Applicants: Fabien Chojnowski, Roanne (FR); Yuri Peter Kizimovich, Westlake Village, CA (US); Frederic Tachet, Saint Leger sur Roanne (FR); Remy Blanchard, Roanne (FR); Boris Basevich, Sunnyvale, CA (US)

(72) Inventors: Fabien Chojnowski, Roanne (FR); Yuri Peter Kizimovich, Westlake Village, CA (US); Frederic Tachet, Saint Leger sur Roanne (FR); Remy Blanchard, Roanne (FR); Boris Basevich, Sunnyvale, CA (US)

(73) Assignee: Nettelo Incorporated, Westlake Village, CA (US)

( * ) Notice: Subject to any disclaimer, the term of this patent is extended or adjusted under 35 U.S.C. 154(b) by 0 days.

(21) Appl. No.: 16/654,185

(22) Filed: Oct. 16, 2019

(51) Int. Cl.
| | |
|---|---|
| *G06T 17/00* | (2006.01) |
| *A61B 90/00* | (2016.01) |
| *G06F 3/01* | (2006.01) |
| *G06T 7/10* | (2017.01) |
| *G06K 9/46* | (2006.01) |
| *G06T 7/50* | (2017.01) |
| *G01B 11/03* | (2006.01) |

(52) U.S. Cl.
CPC .............. *A61B 90/36* (2016.02); *G01B 11/03* (2013.01); *G06F 3/011* (2013.01); *G06K 9/46* (2013.01); *G06T 7/10* (2017.01); *G06T 7/50* (2017.01); *G06T 17/00* (2013.01); *A61B 2090/367* (2016.02); *A61B 2562/0219* (2013.01); *G06T 2200/08* (2013.01)

(58) Field of Classification Search
CPC .............. A61B 90/36; A61B 2090/367; A61B 2562/0219; G06T 7/10; G06T 7/50; G06T 17/00; G06T 2200/08; G01B 11/03; G06F 3/011; G06K 9/46
See application file for complete search history.

(56) References Cited

U.S. PATENT DOCUMENTS

| | | | |
|---|---|---|---|
| 2011/0148875 A1* | 6/2011 | Kim ........................ | G06T 13/40 345/420 |
| 2014/0176565 A1* | 6/2014 | Adeyoola ........... | G06F 16/5854 345/473 |
| 2019/0231433 A1* | 8/2019 | Amanatullah ..... | A61B 17/1703 |

* cited by examiner

*Primary Examiner* — Chong Wu
(74) *Attorney, Agent, or Firm* — Nadya Reingand; Yan Hankin

(57) ABSTRACT

A 2D camera is used to create a 3D full body image. A camera takes one 2D image, an accelerometer is used to calculate camera position, and several computer systems are employed to construct a 3D body model. This may be performed in a non-controlled environment and by the user alone. An automatic segmentation of the 2D image creates special information for 3D model reconstruction. Once the 3D model measurements are extracted, the user has the option to further specify measurements. In one embodiment, the 3D model is shared via cloud and social media, and also used to assist in shopping while ensuring accurate measurements for the user. In another embodiment, the digital model of products designed for the target consumer body is automatically adjusted and shown as a 3D image on the user's body. The 3D model may be shared with businesses for manufacturing using 3D morphology.

6 Claims, 22 Drawing Sheets

SINGLE IMAGE MOBILE DEVICE HUMAN BODY SCANNING AND 3D MODEL CREATION AND ANALYSIS

FIELD OF THE INVENTION

The present invention is in the field of creating and analyzing 3D models of the human body with mobile devices from 2D images captured by device's single camera.

BACKGROUND OF THE INVENTION 3D cameras, as disclosed in the current state of the art, are not required by the present invention. A 2D camera is different from a 3D camera as a 3D camera consists of either: (1) two 2D cameras and special hardware to synchronize the images obtained via the 2D cameras; (2) one 2D camera plus infrared sensors; or (3) other technology comprising an array of sensors. 3D cameras use both image capture and creation of a depth map of the image. The present invention does not require a depth map of the image. 3D cameras are not included in the mass market available for mobile devices, except in some niche markets, so most mobile devices only comprise an included 2D camera.

The mass market available to most mobile device does not currently provide a solution to scan/image a human body using a 2D camera to create and analyze a human 3D body digital model, as well display it in 3D and share the 3D object in a web-enabled 3D format, providing an ability to access it with full 3D visual and metric information from any device, anytime, and anywhere. The present invention addresses this problem.

SUMMARY OF THE INVENTION

The invention uses any 2D camera for the purpose of performing 3D full body self-scanning and body metrics analysis. A mobile device camera, for example, may take 2 or more, or 3 or more, 2D images, while the mobile device's accelerometer is used to determine the angular camera position. This information is shared with a CPU processor (cloud, server, etc.) to form an accurate 3D body model of a user. These steps may all be performed in a non-controlled environment (for an example home conditions) and in self-mode (i.e., performed by the user alone). The method further comprises performing an automatic segmentation of the 2D images to create a 3D model reconstruction, which can be further adjusted by the user. Once the 3D model is created, measurements are automatically extracted and the user has an option to further select or specify measurements to be extracted. In one embodiment, the 3D model is shared via cloud and social media, and it is also used to assist in shopping while ensuring accurate measurements for the particular user. In another embodiment, the digital model of one or more products designed for the target consumer body may be automatically adjusted and shown as a 3D image on the target consumer's 3D body image. Optionally the 3D model may be directly shared with businesses for traditional or additive manufacturing (e.g., 3D printing) of the made-to-measure clothing or any special medical/sport product using 3D morphology and precise measurements of the consumer's body or particular body parts (legs, arms, etc.).

In some aspects, the method for creating one or more 3D images of a user comprises placing a 2D camera on a planar surface, capturing a first 2D image of the user, capturing a second 2D image of the user, the second 2D image being a different perspective than the first image, the user remaining on a single axis in both images, segmenting the first and second images to form a plurality of segmented 2D images, constructing a 3D image from a combination of all three of the plurality of segmented images, data extracted from that plurality of images, and information on camera position and angle, however slight.

In some aspects, an additional method for creating one or more 3D images of a user comprise placing a 2D camera on a planar surface or holding the 2D camera, capturing one full body length 2D image of the user standing and facing the camera (user should be wearing tightly fitting, i.e. form-fitting, clothes), forming a plurality of segmented 2D images from the one full body length 2D image, constructing a 3D image from a combination of data extracted from the plurality of segmented 2D images and data determined based on the 2D camera's position and its angle relative to a control angle (e.g., the ground).

In some aspects, an additional method for creating one or more 3D images of a user comprises placing a 2D camera on a planar surface or holding the 2D camera, capturing one full body length 2D image of the user standing and facing the camera, wherein the user is wearing any casual (i.e., non form-fitting) clothing, forming a plurality of segmented 2D images from the single full body length 2D image, constructing a 3D image from a combination of data extracted from the plurality of segmented 2D images and information obtained on the camera's position and angle relative to a control angle (e.g., the ground).

In some aspects, the method further comprises the step of manually adjusting the data extracted from the plurality of segmented 2D image, wherein the manual adjusting is performed by the user.

In some aspects, the method further comprises the step of automatically extracting measurements of the user's body from the 3D image constructed.

In some aspects, the method further comprises the step of adding one or more desired measurements for user height based on the 3D image.

In some aspects, the method further comprises the step of adding one or more desired measurements for user girth based on the 3D image.

In some aspects, the method further comprises the step of adding one or more desired measurements for a geodesic distance between two or more points on the user's 3D image.

In some aspects, 2 or more 3D images are constructed, and the method further comprises the step of saving each 3D image such that the user may track one or more bodily features over time.

In some aspects, the 3D image is compared to an ideal 3D model.

In some aspects, the method further comprises the step of sending measurements to an authorized recipient.

In some aspects, the method further comprises the step of tailoring an outfit for the user based on measurements sent to an authorized recipient.

In some aspects, the method further comprises the step of comparing the extracted measurements to known fitment data of a desired product.

In some aspects, the method further comprises the step of suggesting a product based on information retrieved from a comparing step.

In some aspects, the geodesic distance is the distance between the ground and a point on the circumference of the user's body.

In some aspects, the method further comprises the step of measuring, using a virtual measurement tape, a distance between two points on the 3D image.

In some aspects, the method further comprises the step of measuring a circumference of the user's body.

In some aspects, the method further comprises the step of controlling a camera position using an accelerometer coupled to the camera.

In some aspects, the method further comprises the step of generating feedback using an accelerometer coupled to the camera, the feedback correcting the user's positioning.

In some aspects, the computed camera position is obtained via an accelerometer coupled to the camera, the computed camera position comprising the camera's sensor plane position relative to the user.

In some aspects, the method further comprises measuring one or more dimensions comprising depth.

In some aspects, the method further comprises the step of creating a real time transformation of the user's body, said real time transformation being designed exactly once per categorical body type. The real time transformation may then be used without further input to test varying garments or other wearable products on the user's particular body in a virtual manner.

BRIEF DESCRIPTION OF THE DRAWINGS

The present invention will now be discussed in further detail below with reference to the accompanying figures in which:

FIG. 17A shows an example for legs. FIG. 17B simplifies the example shown in FIG. 17A to correspond with points A, B, C, and D, as discussed herein. It is noted that A, B, C, and D, as discussed herein, relate to either one of the limbs of a user's body. A1 through D1, as discussed herein, are different and correspond to correlating points on a projected profile after A through D have been determined on the images.

DETAILED DESCRIPTION OF THE PREFERRED EMBODIMENT

Figure 1:
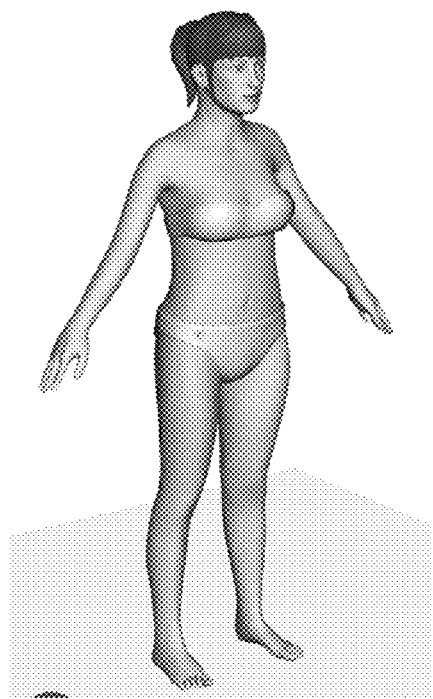
FIG. 1 shows an example of a 3D model created by the method of the present invention.

The invention comprises a method which uses a single 2D camera, for example, a mobile device's camera, to take multiple (i.e., two or more) 2D pictures and make a 3D body model. The method requires 2 images of a body, from which the method creates a 3D model, and without requiring a depth measurement. The camera is ideally built-in to the mobile device. In one embodiment the camera is external to the mobile device and connected via a wired or wireless connection. The mobile device is ideally a smartphone, PDA, tablet, or other small mobile device, but it could also be a laptop, desktop computer, or other device equipped with a camera. For higher accuracy of the 3D reconstruction, invention may further comprise using a built-in accelerometer providing angles for camera positioning. In some embodiments, the method comprises taking three or more 2D pictures to form a 3D body model.

During initial 2D image capture, the subject is positioned in two poses (manners) in front of the camera in an uncontrolled (e.g., home) environment: the first pose may be, e.g., a front image, and the second pose may be, e.g., a side image (profile). In the case of substantial limb symmetry, the subject may be positioned in a third (i.e., the other side, left or right) position. The subject may further turn from a first pose to a second pose via a conventional body rotation around a single axis, such as a vertical axis. A sequence of the two images is captured for construction of a 3D model. Only two positions and two pictures are generally needed for construction of a 3D model. The camera may be programmed with an application and/or timer which provides the subject with enough time to change positions. The key is that any conventional 2D camera may be used from any mass market device, and usually the camera is incorporated into a mass market mobile device. The 2D images are captured in any uncontrolled environment (basic lighting conditions, no special background or other special conditions for image taking environment). The device may be, e.g., placed on a plane surface and the subject stands in front of the camera. No special conditions or extra equipment, calibration landmarks, or other information, equipment, or technology is needed. The image capture can be performed in a home environment with any mobile device and personally by the subject/user. During image capture, the user is ideally wearing tight, form-fitting clothing, underwear, or no clothing, so as to facilitate the best possible measurements and creation of the most accurate 3D model.

A 3D camera is not required for formation of a 3D image. A 2D camera is different and simpler than a 3D camera, as a 3D camera consists of either: (1) two 2D cameras and special hardware to synchronize the images; (2) one 2D camera plus infrared sensors; or (3) some other technology as an array of sensors. 3D cameras use both image capture and creation of a depth map of the image. The present invention does not require a depth map of the image. 3D cameras are not included in the mass market available for mobile devices, except in some niche markets, so most mobile devices only have an included 2D camera. The present invention allows for creation of 3D images using 2D cameras, wherein the camera is required to take only two 2D images. It should be noted that, in some embodiments, although not required, the method may further comprise obtaining a depth map of the pictures taken, which would allow the method to be applicable to devices comprising 3D cameras. The depth map would allow for further initial image processing.

The present invention may further use an accelerometer incorporated in the mobile device to control camera position and generate feedback, if necessary, to correct user positioning. The present invention may also use an accelerometer incorporated in the mobile device (or otherwise coupled to the camera) to compute a camera's sensor plane position relative to the subject/user in a 3D coordinate system to allow for a full 3D reconstruction including a calculation of the depth. The mobile device in the present invention may also compute camera calibration, including the exact spatial position of the camera, using a user's height as a parameter in combination with the obtained accelerometer data. The present invention then also obtains 3D coordinates of the set of body feature points using the camera calibration data.

The present invention further discloses methods for creating a 3D model from only one full body length 2D image of the subject, wherein the subject is wearing tight (i.e. form-fitting) clothing and standing facing the 2D camera.

The present invention further discloses methods for creating a 3D model from only one full body length 2D image of the subject, wherein the subject is wearing arbitrary or casual (i.e. non form-fitting) clothing and facing the 2D camera.

The method of the present invention can obtain and tune a mathematical model of the 3D free form deformation of a standard human body 3D explicit model. Such a 3D free form deformation is obtained from pre-calculated and stored data which is adapted to the current body using a special set of universal 3D shape functions. The method of the present invention doesn't require any databases of human shape data and/or any related statistical data. A single explicit 3D description of one example for a male and one example for a female is all that is required. The present invention uses a 3D body explicit shape data super compression technique to work with a data size of 50-100 kB for the full 3D body image and for communication between a client device and a cloud/server for storage. The mobile device can be in communication with a cloud storage server via a wireless or wired network connection. A cloud-based computational facility can be established to accelerate computations necessary to solve minimization problems related to 3D shape recovery, which allows for use of the method with a wide spectrum of mobile devices without requiring a high device processing power. The present invention may further include providing an interface for interactive feedback from the user. The user can use this interface in order to more tightly fit the model to their 2D images, as well as interact with an application which has social media, shopping, history, and other features. The user can tailor feedback to fit the images to their body for greater precision of the 3D model reconstruction and has the ability to use images taken without special provisions for conditions such as background contrast, lighting, etc.

The present invention allows for 3D image capture anytime and anywhere, via use of a 2D camera; the ability to capture, store, and automatically calculate body metrics, which may be displayed and labelled in a 3D image created from 2D images; the ability to perform additional body 3D analysis; and the ability to access and share 3D digital models of the user's human body as a customer when shopping. The present invention further allows makers of clothing or medical/sport wearable products to access customer body metrical and morphological data, customize products, and improve products, and gather feedback on the product, all potentially before the product is even manufactured.

The present invention further stores and tracks a history of 3D models of a user's body. This means a user is able to follow changes in shape, size, and other body metrics, using the history of 3D models. This feature has applications for fitness and health tracking, tracking growth, and so on. The present invention allows a user to share their 3D models with other users and via social media. The present invention also allows a user to compare their model to an ideal model. This feature can be used by a user who has an ideal body shape they are attempting to achieve and allows the user to track progress while they move toward that ideal shape.

The present invention also allows for the user to zoom in and out of their 3D model and to rotate their 3D model as they desire.

The present invention allows automatic computations of the body measurements from the 3D model. Users may view and interrogate, in 3D, any measurement taken from the computed 3D digital body using virtual measurement tape. In addition, any 3D body measurement presented as a body circumference, length between two circumferences, length between a circumference and the floor, or a geodesic distance between 2 or more points selected by the user on the 3D digital body, may be computed and stored in real time. These measurements can then be used to determine a clothing fit or size. This feature allows a user to use a digital 3D model to facilitate purchase or alteration of clothing. The present invention provides, if desired, sizing information for multiple clothing sizing system, international and otherwise, in combination with the display of the 3D image of the customer body on personal devices or any device connected to the Internet. The present invention can be used with any manufacturer's sizing or measurement information in order to determine if a desired item will fit and whether the fit will be tight, loose, etc. The present invention also provides a fit index computation and may display the index computation on the 3D image of the customer body.

The present invention further allows the 3D model to be directly shared with businesses for traditional or additive manufacturing (3D printing) of custom-made clothing or any special medical/sport product using 3D morphology and requiring precise measurements of the customer body or body parts (such as legs, arms, etc.).

The present invention further allows for the creation of an implicit model of the subject's body along with an explicit body surface presentation, based on a set of special shape functions. Such a model may be used for real time transformation of 3D models of products (e.g., clothes, special medical and sports wearables) in order to fit a particular subject's body. The product may be tested and/or custom-designed to fit to the particular user's body by combining information on a categorical body shape and information from the 3D image obtained via the method described above, in order to instantaneously and virtually examine the product on the user for style, fit, etc. A 3D image and correspondent mapping function is obtained via the method described above, which further allows for the creation of a real time transformation of 3D models of varying products (e.g., clothes, special medical, sports wearables, etc.) in order to fit a particular subject's body. The virtual product (which is designed once for a categorical (i.e., particular) body) may be tested and custom-designed to fit to the particular user's body by combining information on the product designed for a categorical body shape and information from the 3D image obtained via the method described above. Thus, the product may be instantaneously and virtually examined as a 3D image (3D product on the 3D user) for style, fit, etc.

FIG. 1 shows an example of a 3D image which is constructed according to the method of present invention.

Figure 2:
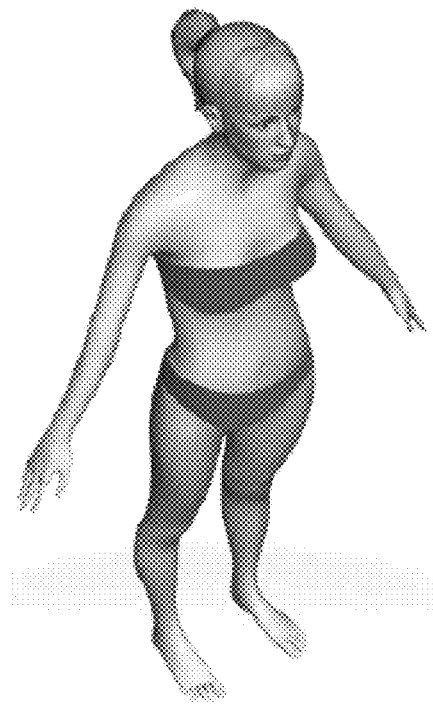
FIG. 2 shows an example of a view due to manipulation and rotation of a 3D model.

FIG. 2 shows an example of how a user may manipulate and rotate a 3D model created by the method of the present invention. FIG. 2 shows an angular view from a point above the subject's image. Essentially, the present invention allows for a user to rotate and view the 3D image in any manner in order to see particularly desired aspects of their body.

Figure 3:
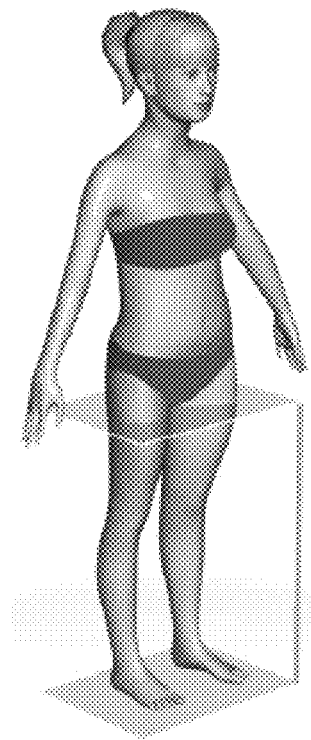
FIG. 3 shows an example of a user's measurement extracted from a 3D model. This particular example shows a specific circumference of a user's body being measured, as well as a distance being measured from the ground to the particular circumference of a user's body.

FIG. 3 shows an example of a user's measurement extracted from a 3D model. This particular example shows a specific circumference of a user's body being measured, as well as a distance being measured from the ground to the particular circumference of a user's body. This figure further shows yet another view of the same body as FIG. 2., rotated as desired by the user.

Figure 4:
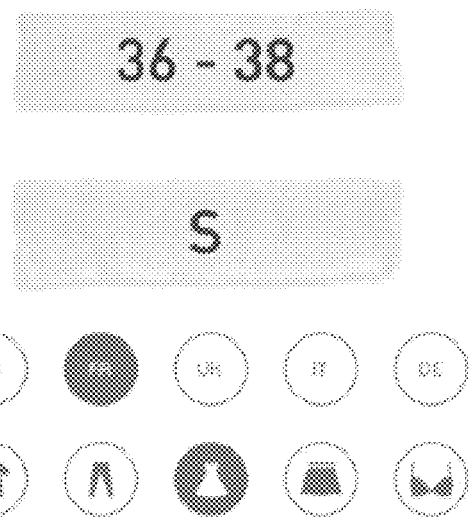
FIG. 4 shows an example of a user interface with exemplary extracted measurement information.

FIG. 4 shows an example of a user interface according to the present invention, with exemplary extracted measurement information. The information depicted comprises a size range, a size category (small, or "s"), choice of country for correct reference, and type of clothing. In this case the options displayed correspond to a female, but male options are similarly available.

Figure 5:
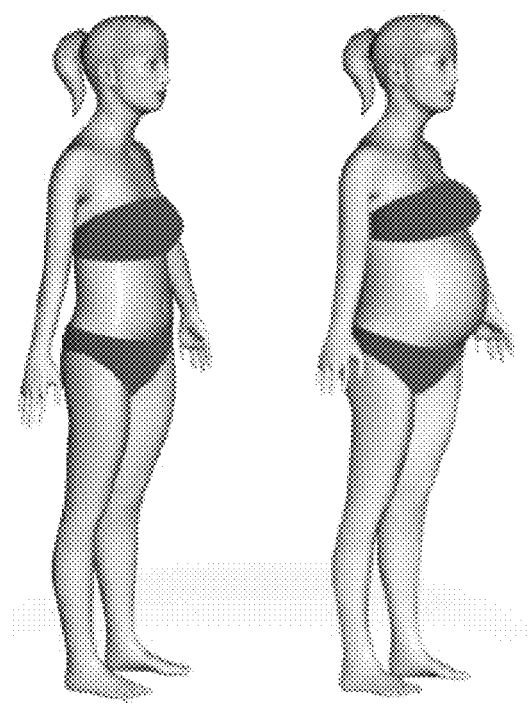
FIG. 5 shows an example of a history of 3D models for a user to compare.

FIG. 5 shows an example of a history of 3D models for a user to compare. In this particular example, a woman is depicted in two images. In the first image, the woman is imaged as prior to/after pregnancy, while in the second image, the same woman is imaged as pregnant. Such images were obtained at different times but both are saved by the invention such that comparisons may be made whenever desired by the user in order to track progress.

Figure 6:
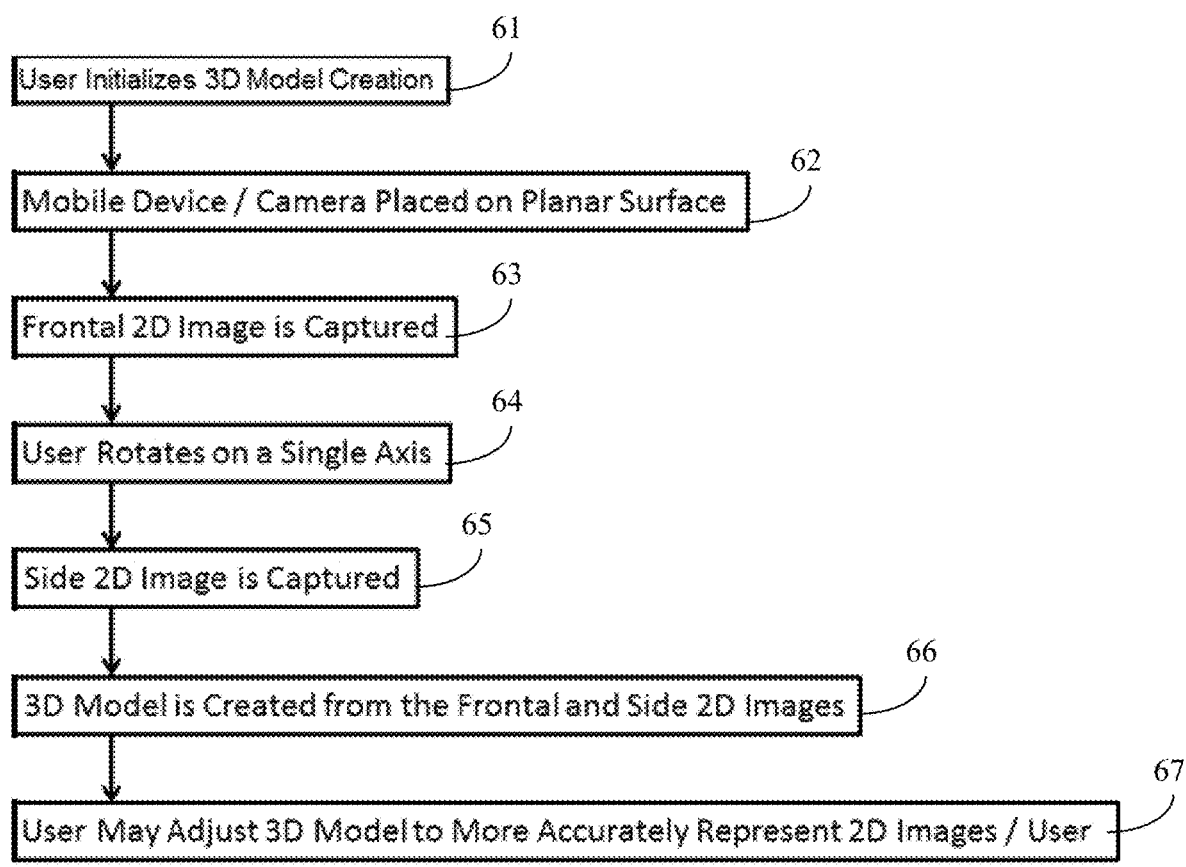
FIG. 6 is a flowchart demonstrating one method of 3D model creation according to the present invention.

FIG. 6 is a flowchart demonstrating one method of 3D model creation according to the present invention. In the method according to FIG. 6, a user first initializes the 3D model creation (e.g., by opening/starting the program) 61. Then, the user places the mobile device/camera on a planar surface 62. A frontal 2D image is captured 63, then the user rotates on a single axis 64, and when the user reaches a side view (relative to the camera), a side 2D image is captured by the camera 65. Once both images are captured, a 3D model is generated from the two images 66. The user may also further customize the created 3D image to adjust and more accurately represent the dimensions of the user 67.

Figure 7:
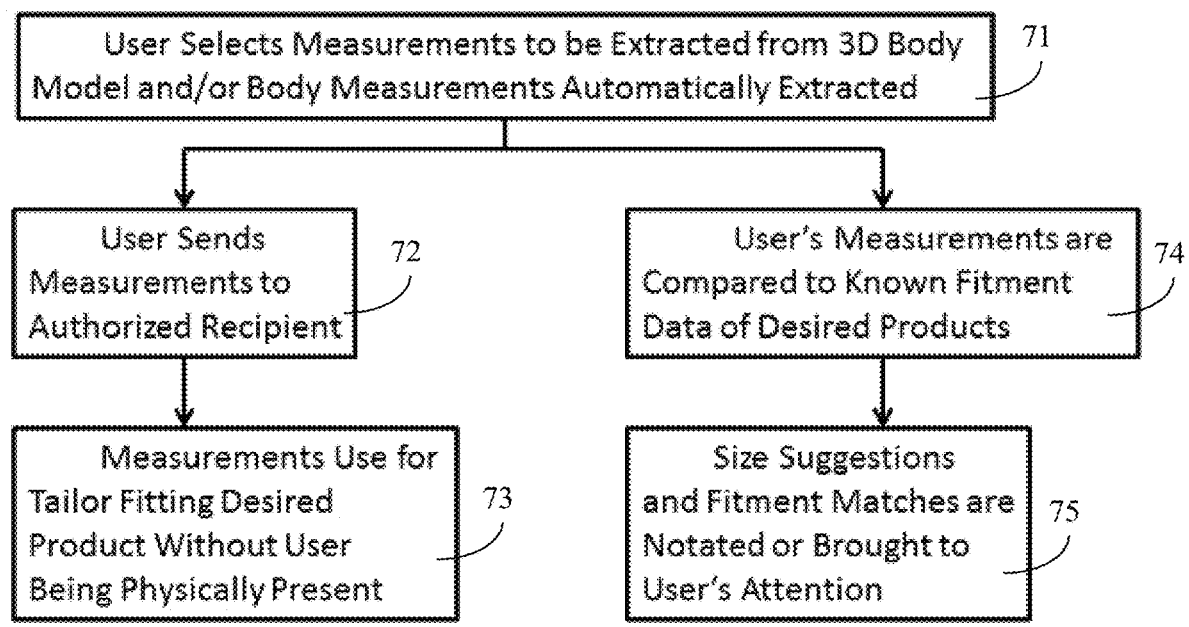
FIG. 7 is a flowchart demonstrating one method for measurement extraction from a 3D model according to the present invention.

FIG. 7 is a flowchart demonstrating examples of measurement extraction from a 3D model according to the present invention, and particular applications for the extracted information. For example, via the interface, a user may select particular measurements to be extracted from the 3D body image/model, or alternatively, body measurements are automatically extracted by the program 71. From this point, the user may send measurements to an authorized recipient 72, and the measurements may be used for tailoring or fitting a particularly desired product without requiring the user to be physically present for fitting 73. Alternatively, the user's measurements may be compared to known fitment data of particularly desired products 74, after which, based on the comparisons performed, size suggestions and fitment matches are notated or brought to the user's attention 75.

Figure 8:
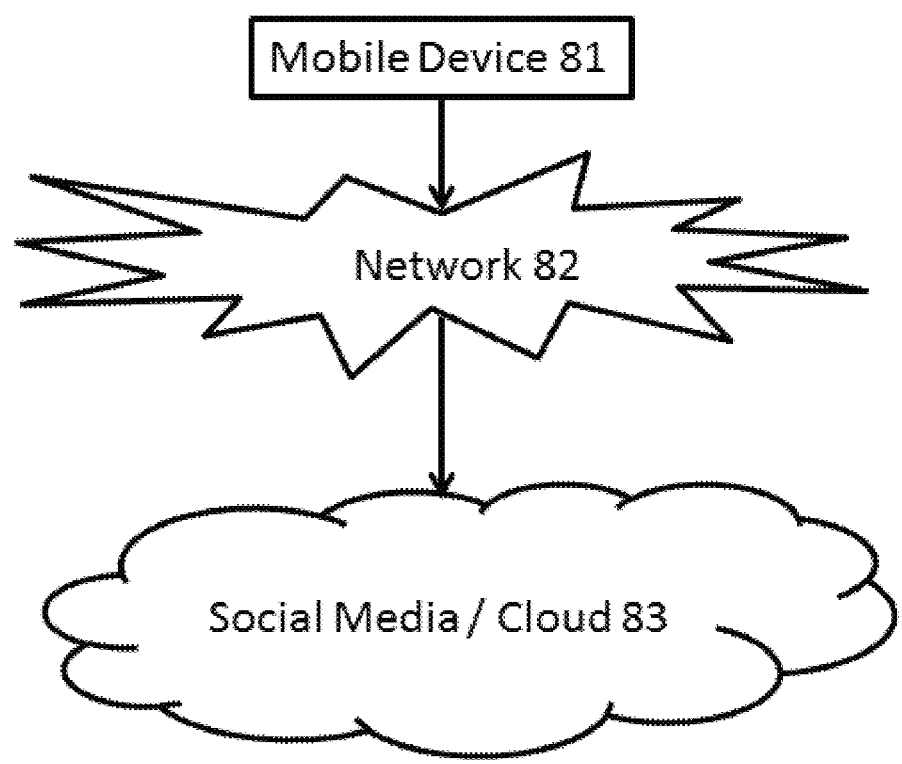
FIG. 8 is a flowchart demonstrating an exemplary connection of a mobile device with social media or a cloud server according to the present invention.

FIG. 8 is a flowchart demonstrating an exemplary connection of a mobile device with social media or a cloud server according to the present invention. The mobile device 81 is connected to a network 82, which in turn is connected to a social media server or cloud server 83.

Figure 9:
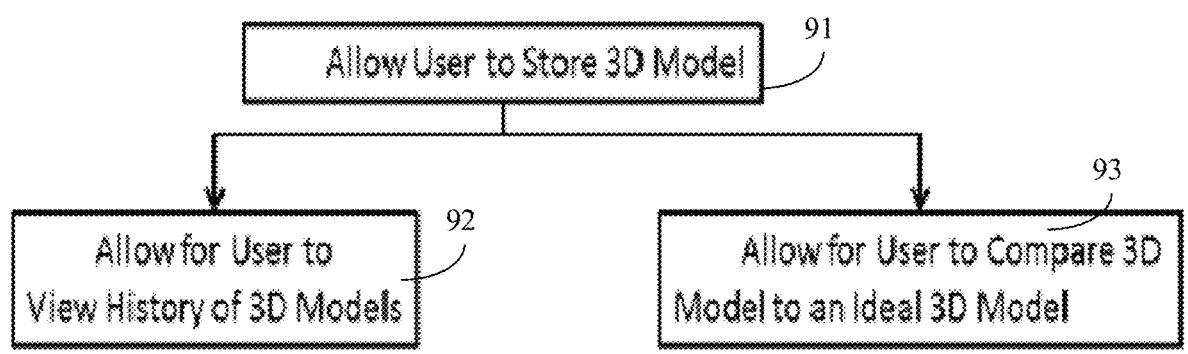
FIG. 9 is a flowchart demonstrating exemplary storage features for 3D models according to the present invention.

FIG. 9 is a flowchart demonstrating exemplary storage features for 3D models according to the present invention. Examples of applications comprising the ability to store various 3D models of a user's body through time 91 include but are not limited to allowing the user to view a history of 3D models to track progress 92, and allowing the user to compare 3D models of the user's body relative to an ideal 3D model 93.

Figure 10:
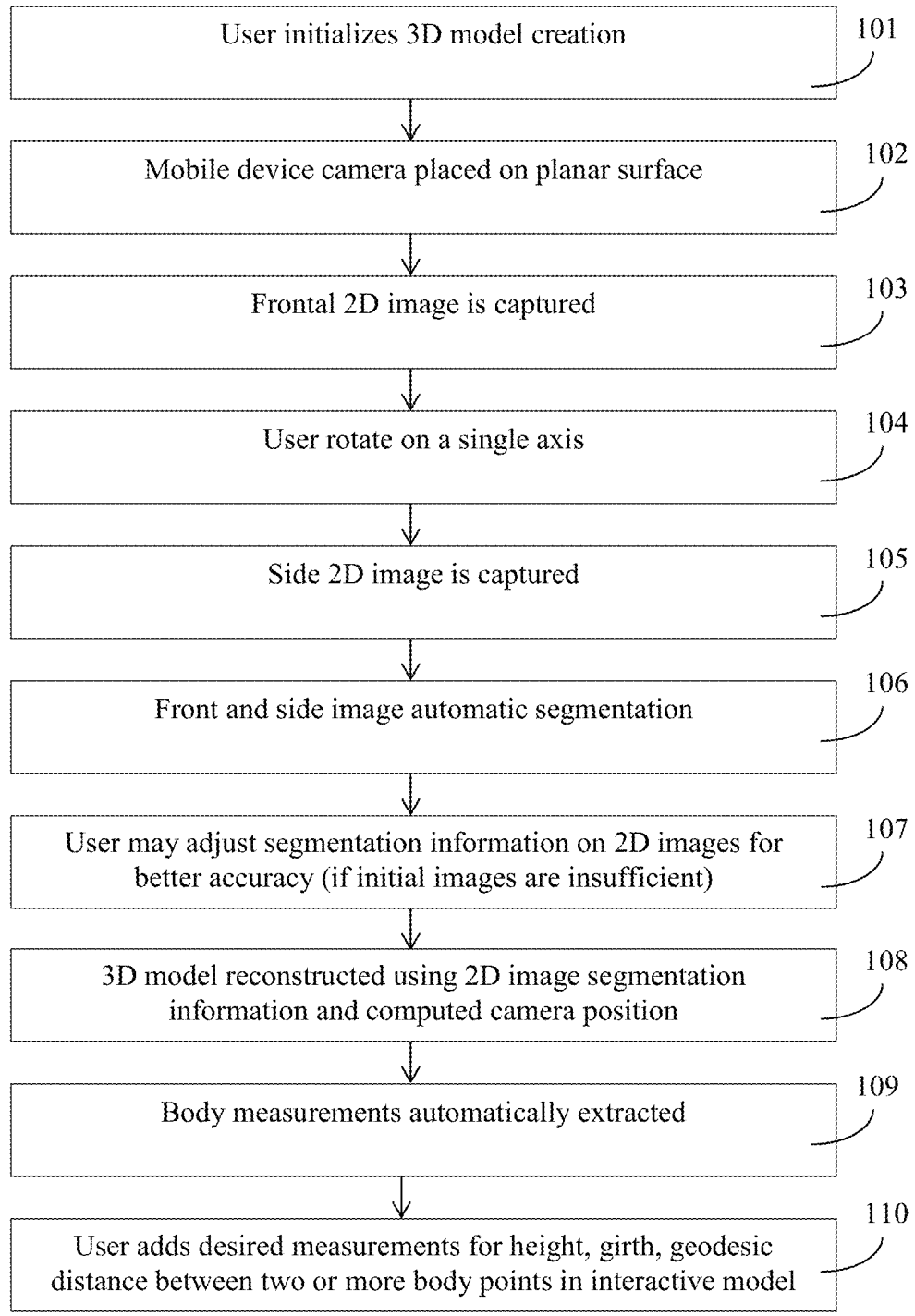
FIG. 10 is a flowchart demonstrating another exemplary 3D model creation and measurement extraction according to the present invention.

FIG. 10 is a flowchart demonstrating another example of 3D model creation and measurement extraction according to the present invention. First, a user initializes the 3D model creation 101. Then, the camera is placed on a planar surface 102. A frontal 2D image is captured first 103, the user rotates on a single axis 104 until the camera can capture a side 2D image 105. Then, the front and side images are automatically segmented 106. The user may adjust segmentation information on the 2D images for better accuracy 107, especially if the initial two images are insufficient to accurately represent the user in 3D. Then, a 3D model is reconstructed using the 2D image segmentation information and the computed camera position 108. Body measurements are then automatically extracted 109, and the user may add desired measurements for height, girth, and/or geodesic distance between two or more body points in the interactive 3D model 110.

Figure 11:
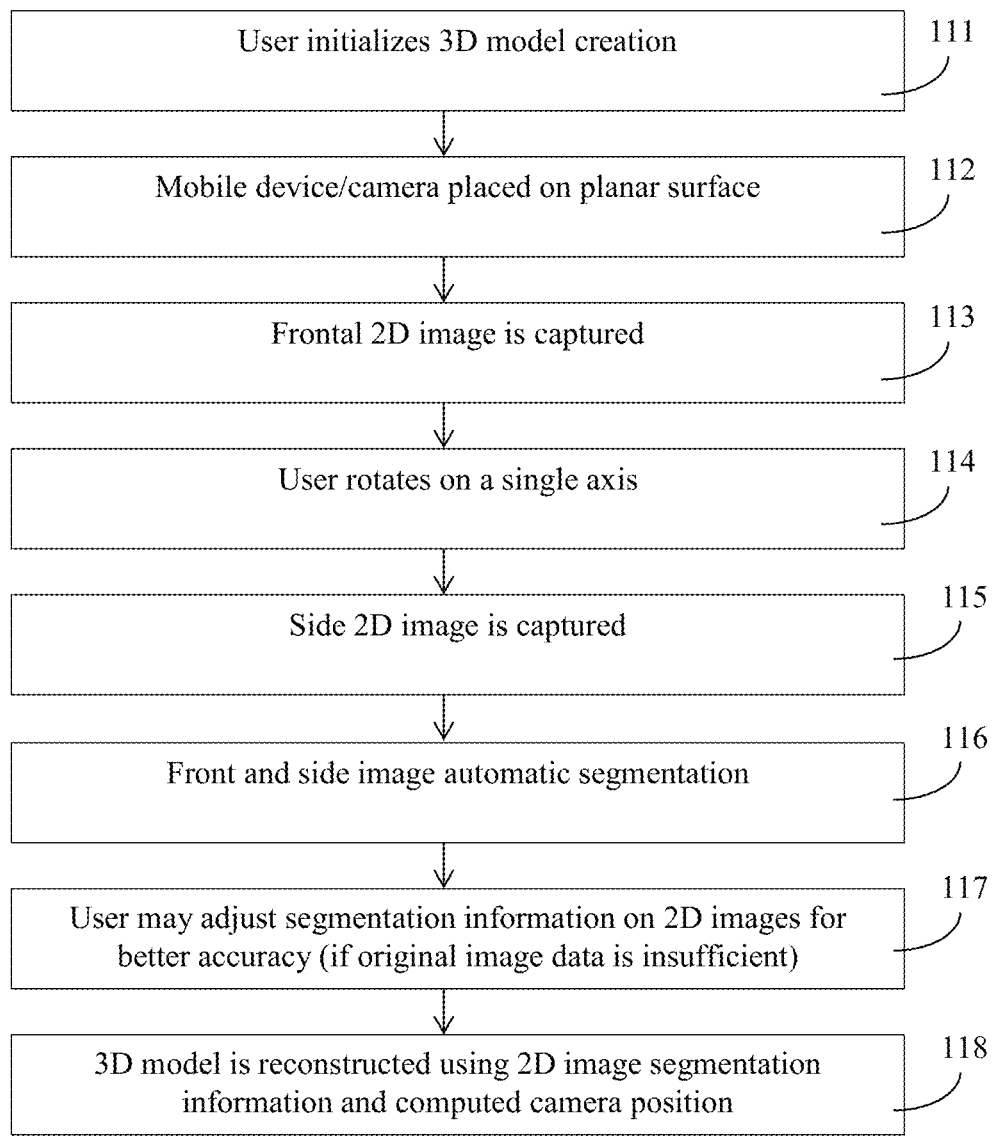
FIG. 11 is a flowchart demonstrating an exemplary 3D model creation and construction according to the present invention.

FIG. 11 is a flowchart demonstrating another example of 3D model creation and construction according to the present invention. In this example, the user initializes the 3D model creation 111. Then, the camera is placed on a planar surface 112. A frontal 2D image is captured first 113, the user rotates on a single axis 114 until the camera can capture a side 2D image 115. Then, the front and side images are automatically segmented 116. The user may adjust segmentation information on the 2D images for better accuracy 117, especially if the initial two images are insufficient to accurately represent the user in 3D. Then, a 3D model is reconstructed using the 2D image segmentation information and the computed camera position 118.

Figure 12:
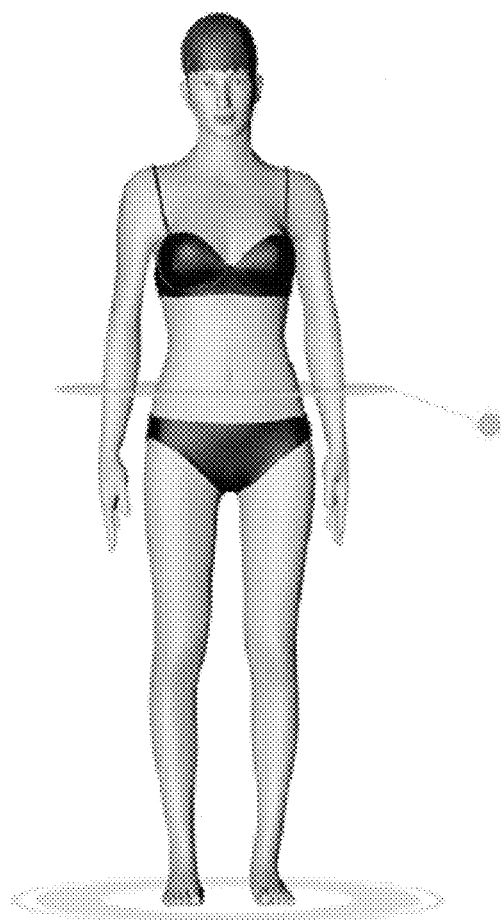
FIG. 12 shows an example of a frontal image of a 3D image created by the present invention.

FIG. 12 shows an example of a frontal image of a 3D image created by the present invention. This virtual product, with or without a garment, is made possible by the present invention, and each such image is required to be designed exactly and only once for a categorical body. The 3D image created may be tested or further customized to fit the particular subject's body by combining information on a product (e.g., a garment) designed for a categorical body shape with information from the 3D image of the subject (obtained as described herein). Thereafter, the product can be instantaneously and virtually examined on the subject for style. Alternatively, the user may similarly examine the subject body without a garment (e.g., for fitness purposes).

Figure 13:
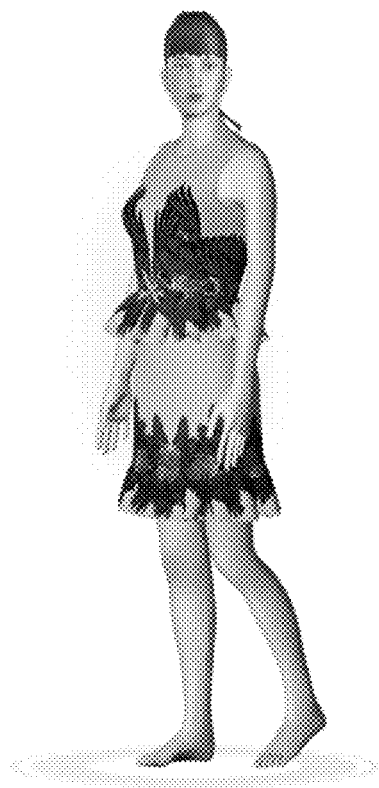
FIG. 13 shows an example of an image of a user comprising a piece of clothing on the user's body and a virtual representation of how that piece of clothing would look on the user.

While FIG. 12 shows a 3D image of a subject without a garment, FIG. 13 shows an example of a 3D image of a digital model of a garment on the same user's body, i.e. a virtual and instantaneous representation of how that piece of clothing would look on the user. The garment is designed for a categorical body shape and reflects specific designs intended, such as style, body lay out, etc. The user instantly sees a 3D image of the garment on her body while all original design intentions and proportions are preserved in the image, making it optimal and realistic. This is due to a revoked mapping between the user's body information obtained and stored and the categorical body information used and stored for design of the garment.

Figure 14:
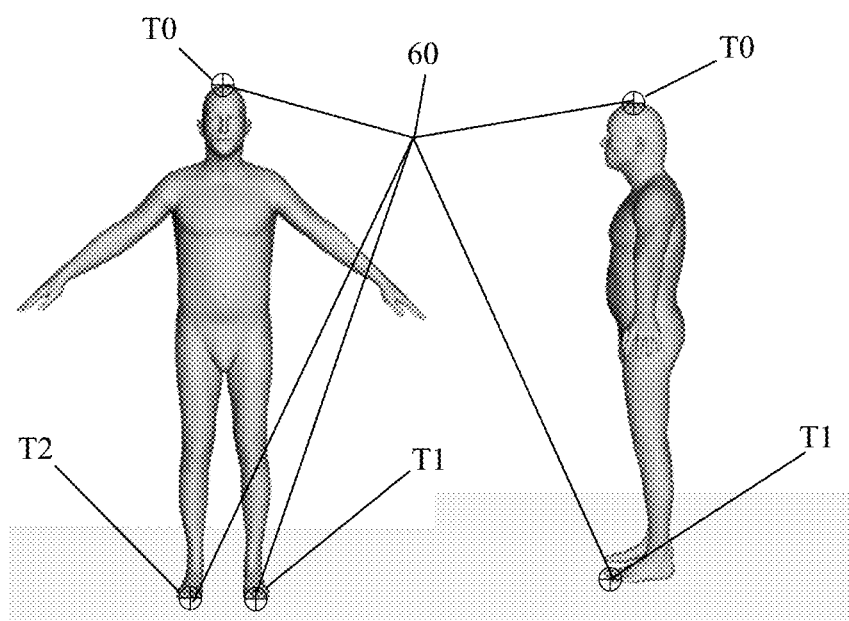
FIG. 14 shows an example of how extremity points are obtained in order to be used for camera calibration (in the form of a computation of the camera's position in 3D) and for the mapping of the extremity points to 3D with known camera parameters and device accelerometer data, using a subject's 2D front and side images as observed from a single fixed spatial position (pinhole), resulting in a set of computed 3D coordinates after camera calibration, according to the present invention.

FIG. 14 shows an example of how extremity points are obtained in order to be used for 3D mapping with known camera parameters and device accelerometer data, using a subject's 2D front and side images, according to the present invention. Such extremity points may be obtained in order to further customize the user's body, as compared to categorical body information.

Figure 15:
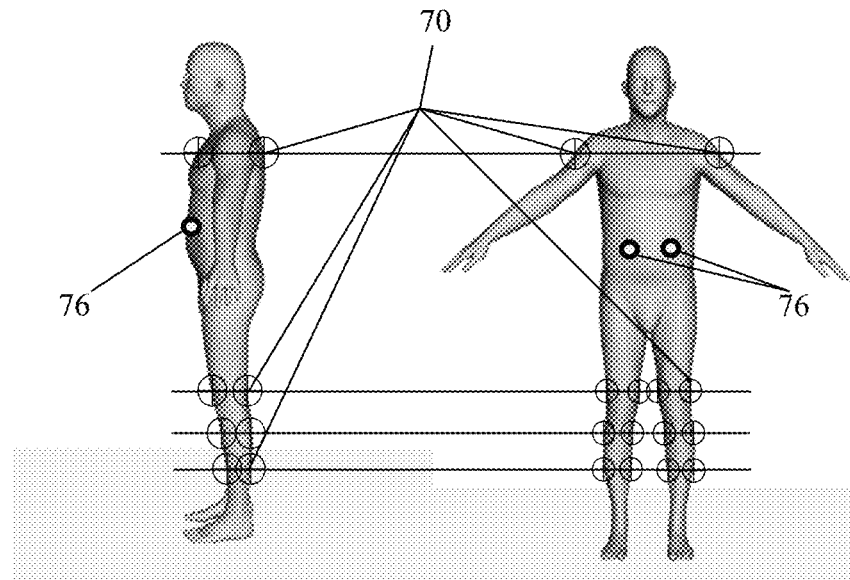
FIG. 15 shows an example of collecting training points and reconstructing their 3D coordinates for computation of the mapping function, $F_m$, using a subject's 2D front and side images, as observed from a single fixed spatial position (pinhole), resulting in a set of computed 3D coordinates, according to the present invention.

FIG. 15 shows an example of collecting training points for computation of the mapping function, $F_m$, using a subject's 2D front and side images, according to the present invention. Such training points may be obtained in order to further customize the user's body, as compared to categorical body information. It should be noted that the mapping function is computed exactly and only once per categorical body type. The unique body type of each user is entered/obtained once, after which the user may try on any clothing/garments to determine how the clothing/garments look on the user in a virtual setting. The only requirement is that the dimensions of the clothing are known or suggested. Such dimensions may be entered by the designers of the clothing/garments and are generally easily obtainable. Thus, a user may try on any garment on which information is available, and designers of garments and other wearable products may receive information from the users of the method for additional feedback (e.g., transforming garments to fit different categorical bodies, determining whether clothing designed for a particular body type may also look well on other body types previously not considered, etc.). The key feature which makes such functionality, analysis, and adaptability possible is the relative mapping functions obtained and employed by the method.

The following example provides one embodiment of the present invention:

Example 1. A 3D image of a subject/user is obtained via the following steps:

Step 1. The subject uses a mobile device (e.g., smartphone) to make a self-scan in uncontrolled conditions using an application on the mobile device.

Step 2. The mobile device is placed on any plane surface, preferably a flat surface.

Step 3. The subject stands between 2 and 2.5 meters away from the mobile device and facing the front of the camera located on the mobile device. If the surface on which the mobile device is placed is not exactly flat, the interface of application located on the mobile device may assist the user to stand approximately parallel to the mobile device's surface. The interface may also assist the subject to be centered for an optimal view and image capture. The camera captures a first 2D image of the subject facing the camera.

Step 4. The subject turns clockwise or counter-clockwise until standing in profile view relative to the camera. The camera then captures a second 2D image of either the left or right profile image of the subject.

Step 5. The subject exits the scene captured by the camera, and the camera captures a background image without the subject in the image. It should be further noted that this step is particularly provided to increase reliability for the image segmentation in order to find image point coordinates as shown in FIGS. 14 and 15.

Step 6. The mobile device application runs one or more image segmentation algorithms, which extract(s) extremity feature points 60 from the front and side images of the subject (top, bottom). See FIG. 14. The image segmentation algorithms further obtain the camera's angular positions using an accelerometer of the mobile device. Using the algorithmic data, the camera's optical data, the photo sensor parameters, and a reported height of the subject, the application runs another set of algorithms/functions which allow for the computation of a sensed camera position and a map between image coordinates corresponding to the extremity points (x, y, z) 60 in a world coordinate system.

Step 7. Further image segmentation allows for segmentation of the front and side silhouettes of the subject, and a map between image coordinates can be constructed as described in Step 6 above, wherein the image coordinates now correspond to boundary points 70 of both silhouettes. See FIG. 15. More points 70 can be included in the set of images (both along the boundary of as well as within the silhouettes), using machine learning on the data base of information from a user's models, wherein relative spatial positions for such points 70 are continuously being analyzed and determined.

Step 8. A model body (test model) with an explicit surface boundary is used. The model body is represented by a polygon mesh for both genders. X1, y1, and z1 coordinate values are obtained for all topological corresponding points using the information from Step 6 and Step 7.

Step 9. A mapping function, $F_m$, is introduced. The mapping function, $F_m$, maps the surface of the test model (the model body) to the subject's body model as a linear combination of the 3D shape functions obtained in Steps 6-8. The function, $F_m$, is used as a free form deformation of the test model to the user body. While being agnostic to the type of free form deformation, the critical part of the present invention lies in the finding of a set of feature and boundary points and computing their 3D coordinates in the world coordinate system using, e.g., a pinhole camera model. Free form deformation functions that can be used include but are not limited to the linear combination of sparse radial shape functions, using known points of the test model and topologically related user points. Each such shape function is defined per a plurality of points, P, from the test model, and matching points P to a plurality of points, P1, from the user points. Hence, the final coefficients in the linear combination of functions define the mapping function, $F_m$.

Step 10. The subject's 3D model is represented by a final function, $F_m$, which transforms the test model surface polygon mesh into a subject's body model surface polygon mesh. The latter can be created on demand and based on various known methods including but not limited to: 3D rendering, body metric analysis, product fit computations, etc. The final function, $F_m$, is created using commonly known optimization methods for the linear combination of free form deformation shape functions to map a data set of the test 3D model points to the correlated data set of user 3D model points, which are reconstructed from scan images to 3D.

It is noted that all 3D body models created via the process described in Example 1 above have a unique mapping function Fm corresponding to a particular general test model. This relationship will further allow for the creation of a 3D image containing all possible mutual mappings inside the data base pertaining to that particular test model.

The following Example, herein referred to as Example 2, provides an embodiment of the present invention which requires only one full body frontal 2D image of the subject wearing tight (form-fitting) clothing:

Step 1. The subject uses a mobile device (e.g., smartphone) to make a self-scan in uncontrolled conditions using an application on the mobile device.

Step 2. The mobile device is placed on any plane surface, preferably a flat surface.

Step 3. The subject stands between 2 and 2.5 meters away from the mobile device and facing the front of the camera located on the mobile device. If the surface on which the mobile device is placed is not exactly flat, the interface of the application located on the mobile device may assist the user to stand approximately parallel to the mobile device's (i.e. camera's) surface. The interface may also assist the subject to be centered for an optimal view and optimal image capture. The camera captures a single full body 2D image of the subject facing the camera.

Step 4. The subject exits the scene captured by the camera, and the camera captures a background image without the subject in the image. This step is particularly provided to increase reliability and accuracy of the image segmentation as discussed herein in order to find image point coordinates as shown in FIGS. 14 and 15 and described hereinbelow.

Step 5. The mobile device application runs one or more image segmentation algorithms, which extract(s) extremity feature points 60 from the captured front image of the subject (top point, bottom point). See FIG. 14. The image segmentation algorithms further obtain the camera's angular positions using an accelerometer of the mobile device. Using the algorithmic data, the camera's optical data, the photo sensor parameters, and a reported height of the subject, the application runs another set of algorithms/functions which allow for the computation of a sensed camera position and a map between image coordinates, the image coordinates corresponding to the extremity points (x, y, z) 60 in a world coordinate system.

Step 6. One or more intelligent computer systems are used to simulate a profile (i.e. side) silhouette of the subject by using the subject's height, weight, and metrical data obtained from the captured frontal image, once its image coordinates are transformed from image coordinates to world 3D coordinates (see FIG. 23). Computer intelligence prediction is used for the profile silhouette of the subject to combine it with a frontal silhouette extracted from the captured 2D frontal image of the subject.

Step 7. Further image segmentation allows for segmentation of the frontal and simulated profile silhouettes of the subject. A map between image coordinates can be constructed as described in Step 5 above, wherein the image coordinates now correspond to boundary points 70 extracted from both silhouettes (see FIG. 15). Additional image points 76 can be included in the set of images (both along the boundary as well as within the silhouettes), using machine learning on the base of information from a user's stored models, wherein the relative spatial positions of such additional image points 76 are continuously analyzed and determined to further the accuracy of the invention.

Step 8. A model body (test model) with an explicit surface boundary is used. The model body is represented by a polygon mesh for both genders. X1, Y1, and Z1 coordinate values are obtained for all topological corresponding points using the information from Steps 6 and 7.

Step 9. A mapping function, $F_m$, is introduced. The mapping function, $F_m$, maps the surface of the test model (the model body) to the subject's body model as a linear combination of the 3D shape functions obtained in Steps 6-8. The function, $F_m$, is used as a free form deformation of the test model to the user body. While being agnostic to the type of free form deformation, the critical part of the present invention lies in the finding of a set of feature and boundary points and computing their 3D coordinates in the world coordinate system using, e.g., a pinhole camera model. Free form deformation functions that can be used include but are not limited to the linear combination of sparse radial shape functions, using known points of the test model and topologically related user points. Each such shape function is defined per a plurality of points, P, from the test model and matching points P to a plurality of points, P1, from the user points. Hence, the final coefficients in the linear combination of functions define the mapping function, $F_m$.

Step 10. The subject's 3D model is represented by a final function, $F_m$, which transforms the test model surface polygon mesh into a subject's body model surface polygon mesh. The latter can be created on demand and based on various known methods including but not limited to: 3D rendering, body metric analysis, product fit computations, etc. The final function, $F_m$, is created using commonly known optimization methods for the linear combination of free form deformation shape functions to map a data set of the test 3D model points to the correlated data set of user 3D model points, which are reconstructed from scan images to 3D.

The following Example, referred to herein as Example 3, provides one exemplary embodiment of the present invention which requires only one full body frontal 2D image of the subject wearing casual (i.e. non form-fitting, arbitrary) clothing:

Step 1. The subject uses a mobile device (e.g., smartphone) to make a self-scan in uncontrolled conditions using an application on the mobile device.

Step 2. The mobile device is placed on any planar surface, preferably a flat surface, for the subject self-scan or alternatively the mobile device is held by an assisting person.

Step 3. The subject stands between 2 and 2.5 meters away from the mobile device and facing the front of the camera located on the mobile device. If the surface on which the mobile device is placed is not exactly flat, the interface of the application located on the mobile device may assist the user to stand approximately parallel to the mobile device's surface. The interface may also assist the subject to be centered for an optimal view and optimal image capture. The camera captures a first 2D image of the subject facing the camera and the subject can be wearing any type of clothing (i.e. form-fitting clothing is not required).

Step 4. Step 5. The mobile device application runs one or more image segmentation algorithms, which extract(s) extremity feature points 60 from the front image of the subject (top, bottom) (see FIG. 14). The image segmentation algorithm(s) further obtain the camera's angular positions using an accelerometer of the mobile device. Using the algorithmic data, the camera's optical data, the photo sensor parameters, and a reported height of the subject, the application runs another set of algorithms/functions which allow for the computation of a sensed camera position and a map between image coordinates and their correlation to the extremity points (x, y, z) 60 in a world coordinate system.

Step 5. One or more intelligent computer systems are used to extract a subject 2D skeleton from the obtained 2D image and determine/compute key points (i.e. human skeleton joint points) 77 in the subject 2D skeleton, once converted into world coordinates using the camera position reconstruction algorithm (see FIG. 24).

Step 6. One or more intelligent computer systems are used to find the best probable match for the target body using a segmented 3D body data collection which comprises input data such as the extracted skeleton key points 77 (points {Si}, see FIG. 26) and the subject's gender, height, and/or weight.

Step 7. The 3D body skeleton and key points, P={Si}, obtained in Step 5, are combined and correlated with the best probable match, Q={Si}, obtained in Step 6, to define a second mapping function, $F_{m2}$, which is used to transform the most probable match model into the actual subject's 3D body, thus forming a 3D model.

The following examples and description are provided to further enable one of skill in the art to perform the steps claimed by the present invention.

The following terms are used hereinafter, as defined below:

A standard simple pin-hole model is used to analyze a camera image projection of an object using the camera's sensor plane.

"F" is referred to as the center point of the mobile device rectangular sensor;

"C" is referred to as the camera lens optical center point;

"e" is referred to as the focal length of the camera;

"F(u, v, w)," are referred to as the camera coordinates system, with u and v in the sensor plane, u being horizontal, v being vertical, and w being backward perpendicular to the sensor plane, such that F coordinates are (0,0,0) and C coordinates are (0,0, −e);

"$P_0xyz$" is referred to as the scene coordinate system, with the point $P_0$ being on the ground, x and z axis in the ground horizontal plane, y vertical upward, and z axis toward the camera; $P_0$, x, y, z is computed in an optimal way by the algorithm of the present invention.

"A" is referred to as the 3×3 direct orthogonal rotation matrix from 'wuv' to 'zxy'; "A" depends only on the rotation angles $\Theta x$ (pitch), $\Theta y$ (roll) and $\Theta z$ (yaw), which can be derived from the mobile device's accelerometer information;

"g" is referred to as the gravity acceleration vector with known gu, gv, and gw camera coordinates provided by the mobile device's accelerometer;

"P" is referred to as a generic point of coordinates (x, y, z) in the Poxyz coordinate system.

"Q" is referred to as the image of P on the sensor plane, with coordinates (u, v, w) in the F(u, v, w) coordinate system.

"a" is referred to as the 3×1 vector coordinates of Q in F(u, v, w)=(u, v, e)', where X' is the transpose of X;

"k" is referred to as a positive real number defined by CP=−k*CQ.

Therefore, if P is in front of the camera, the pin-hole model 3×1 vector equation is:

$$P = C - k \cdot A \cdot a, \qquad (a.1)$$

where P and C are expressed in the scene coordinates ($P_0xyz$) and "." is the product between scalars, vectors, or matrices. The current example looks at Equation (a.1) as 3 scalar equations where A and b are known (inputs), and all other quantities are unknown, the 7 scalar unknowns being Px, Py, Pz, Cx, Cy, Cz, and k.

"T0" is referred to as the top point of the model, i.e. the highest point of the skull of the model "T1" is referred to as the left toe point of the model, i.e., the farthest/extremity point of the left toe T0 and T1 also may refer to the scene 3×1 vectors of their scene coordinates.

T0=: (T0x, T0y, T0z) and T1=: (T1x, T1y, T1z), where=: means 'equal by definition'.

"a0" refers to the side 3×1 camera image vector of P0.

"a1" refers to the side 3×1 image vector of T1.

"a2" refers to the side 3×1 camera image vector of T0.

"a3" refers to the front 3×1 camera image vector of T0.

"a4" refers to the front 3×1 camera image vector of T1.

ai=: (e, ui, vi)' for i=0, 1, 2, 3, 4.

"AS" refers to the 3×3 rotation matrix A for the camera sensor's plane while an image from the side of a user is made.

"AF" refers to the 3×3 rotation matrix A for camera sensor's plane while an image from the front of a user is made.

bi=: AS.ai, for i=0, 1, 2.

bi=: AF.ai for i=3, 4.

"CS" refers to the camera optical center while a picture from the side of a user is made.

"CF" refers to the camera optical center while a picture from the front of a user is made.

CS and CF also mean the scene 3×1 vectors of their scene coordinates.

CF=: (Cx, Cy, Cz)' where Cx, Cy, and Cz are the scene coordinates of CF.

"h" refers to the height of the scanned person in scanning conditions, i.e., barefoot and in a standing normal relaxed posture.

Example of Set of Equations Used. For the 3 points of interest (P0, T0, T1) and each picture (F, S) the pin-hole equation related the 3D point scene coordinates (x,y,z) and its 2D image coordinates in the sensor coordinates system (u,v), is written as follows:

$$P0 = CS - k0.AS.a0 \quad (e.0)$$

$$T1 = CS - k1.AS.a1 \quad (e.1)$$

$$T0 = CS - k2.AS.a2 \quad (e.2)$$

$$T0 = CF - k3.AF.a3 \quad (e.3)$$

$$T1 = CF - k4.AF.a4 \quad (e.4)$$

The above Equations e.0 through e.4 equate to five 3×1 vector equations, or 15 scalar equations. The following information is known or unknown based on the above Equations e.0 through e.4:

By definition, P0=(0,0,0)';

T0 is an unknown 3×1 vector, except for T0y=h, but T0x and T0z are unknowns;

T1 is an unknown 3×1 vector, except for T1y=0, but T1x and T1z are unknowns;

The image of P0 is unknown in the sensor plane, i.e. u0 and v0 are unknown;

The image of the left toe point T1 is known in camera coordinates, i.e., a1 and a4 are known 3×1 input vectors;

Assuming that the image of the top point T0 is known in side camera coordinates, i.e., a2 is a known 3×1 input vector, in front camera coordinates it is preferable to solve for the u3 (horizontal) coordinate rather than the v3 (vertical) coordinate;

It is shown by example further below how to compute the 3×3 rotation matrices, AS and AF, from known gravity coordinates in the device camera sensor coordinates system provided by mobile device accelerometers. Thus, AS and AF are known inputs;

The pin-hole model multipliers ki (i=0 to 4) are all unknown;

The CF coordinates Cx, Cy, Cz, and CS coordinates, CSx, CSy, CSz, are the main unknowns.

At this point, without any additional assumptions, 15 scalar equations and 18 scalar unknowns exist:

k0, . . . , k4, Cx, Cy, Cz, T0x, T0z, T1x, T1z, CSx, CSy, CSz, u0, v0, v3.

In the 3D scanning environment, the camera is not supposed to move during the front and side Images. In fact, the camera is supposed to be fixed and it is the scanned person who is rotating 90 degrees around a fixed point on the floor (P0) located somewhere between the feet and with the image being close to the sensor vertical symmetry axis (u=0). From this assumed information, the following may also be inferred:

$$CS = (Cz, Cy, -Cx) \quad (e.5)$$

Now provided are the (e.0-e.4) 15 scalar equations in 15 scalar unknowns as well as the camera position, Cx, Cy, Cz. After solving this system of equations, one can find the vector of unknowns: {k0, . . . , k4, Cx, Cy, Cz, T0x, T0z, T1x, T1z, u0, v0, v3}, which allows one to conclude camera calibration, resulting in a known camera position, Cx, Cy, and Cz, and 3D coordinates of the key extremity points of the particular user's 3D body.

The camera calibration algorithm is modified to accommodate the above-described methods employing only one 2D image. The workflow is modified as follows: Based on a new value comprising the user's right toe point, "T2":

According to the pin-hole model:

$$T2 = CF - k5.AF.a5 \quad (e.6)$$

3 key feature points are identified, according to FIG. 14: T0=: (T0x, T0y, T0z), T1=: (T1x, T1y, T1z), and T2=: (T2x, T2y, T2z).

By definition: T0x=0, T0y=H (user's height input value), T0z=0, T1y=T2y=0.

Now there are 10 unknown values: {k3, k4, k6, Cx, Cy, Cz, T1x, T1z, T2x, T2z}, and 9 pin-hole equations: e.3, e.4, e.6.

Using general front image requirements for the scanning subject's pose positioning constraints:

$$T1z = T2z, T2x = -T1x \quad (e.7)$$

The number of unknown values can then be reduced from 10 to 8 by a simple substitution of equations e.7 in to equations e.3, e.4, and e.6.

Finally, a unique least squares solution of the camera position reconstruction comprising 9 scalar equations with 8 unknowns is computed from the one captured 2D frontal image coordinates by solving the above-stated 9 equations having 8 unknowns using a conventional least square technique.

3D Reconstruction Algorithm. A Reconstruction Function (RF) is used to compute a 3D point P of the 3D body in world coordinates from corresponding 2D image coordinates Pf and Ps, of such points as seen on front and left-side images of a user:

$$P(x,y,z) = RF(Pf, Ps, CF, CS, AF, AS) \quad (a.2)$$

The RF uses the front and left side camera orientations matrices, AF and AS, and position vectors, CF and CS, with respect to a fixed reference coordinate system. CF and CS are computed by the above camera position computation algorithm. AF and AS are constructed from camera accelerometer generated angle values.

The Reconstruction Algorithm (RF), can be further described as follows:

1) Unknowns: a given point P with unknown world coordinates, x,y,z;

2) Inputs: 2 cameras' known positions, CF and CS (one real camera and one fictitious camera on the side with a camera position, as provided by Equation e.5), and camera orientation matrices, AF and AS;

3) Inputs: u,v coordinates of point P on both front and side images as P is viewed from both cameras simultaneously, and camera focal length, e.

Step 1: Function RF reconstructs x,y,z for the point P.

Step 2: From the front image of P, the following 3×1 vector equation is generated:

$$P = CF - k1 * AF * a1, \quad (a.3)$$

where CF and AF are known, and scalar k1 and vector P are unknown.

Step 3: From the side image of P, the following 3×1 vector equation is generated:

$$P = CS - k2 * AS * a2, \quad (a.4)$$

where CF and AF are known, and scalar k1 and vector P are unknown.

Step 4: Steps 2-3 together form 6 equations in 5 unknowns (P, k1, k2) with possibly no solution because the 2 lines in 3D space CF-P and CS-P will not intersect in general, although they almost intersect. By looking for the unique couple of closest points on both lines, referred to as P1 and P2, where P1 and P2 are the Least Mean Square (LMS) solutions of equations (a.2) and (a.3).

Step 5: Calculate P=(P1+P2)/2, the middle points of P1 and P2.

Solving for (a.3, a.4) is performed by solving the reduced LMS set of 3 scalar equations in 2 unknowns, k1 and k2:

$$k1*b1 - k2*b2 = C, \quad (a.5)$$

where b1=AF*a1, b2=AS*a2, and C=CS-CF are the known 3×1 vectors.

The LMS solution of (a.4) is given by the unique solution of the 2×2 linear equation:

$$B.k = c, \quad (a.6)$$

having unknown column vector k=(k1, k2)', and wherein B=M'M is a 2×2 definite positive matrix with M=[b1,-b2] (i.e. a 3×2 matrix) and M' is the transpose matrix of M (i.e. a 2×3 matrix), and c=M'C.

After solving for k1 and k2 in the above 2×2 linear system (a.6), the closest points on the 2 lines are calculated by:

$$P1 = CF - k1*b1, \text{ and}$$

$$P2 = CS - k2*b2.$$

Finally, the reconstructed point is taken as: P=(P1+P2)/2.

In addition to the RF, reconstruction is further based on the Projection Function, RF~. RF~ is used to compute a 3D point projection into the front and side image coordinates using known camera positions and camera orientations, as follows:

$$Pf(u,v) = RF\sim(P(x,y,z), CF, AF), \quad (a.7)$$

$$Ps(u,v) = RF\sim(P(x,y,z), CS, AS). \quad (a.8)$$

Computation of the Control and Target Point Sets. The set of points corresponding to the target 3D body are configured and further computed based on a control point set defined to the test 3D body; information from a template and user information are gathered from the images and test 3D body, e.g., using the following steps:

First, the test body is positioned according to the global coordinate system, which is defined during the camera reconstruction stage. In addition, the test body is scaled to the target user's height value.

Second, N horizontal cross-sections of the test 3D body are defined by moving a cutting plane y=C (C is a constant value) with a constant increment, starting from the floor (y=0) to T0 (y=Height). See FIG. 18.

Figure 16:
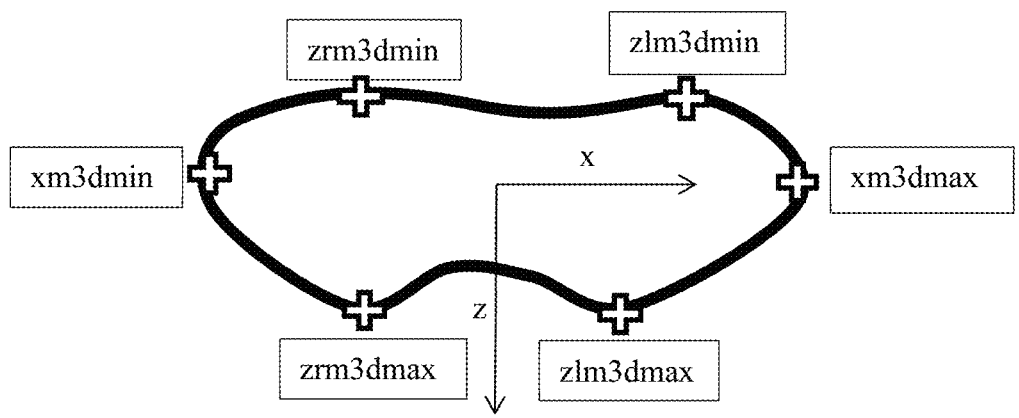
FIG. 16 shows an exemplary 6-point template of a test 3D body shape profile. This template is used to collect {CP} and {TP} point sets for the 3D body torso area.
Figure 17A:
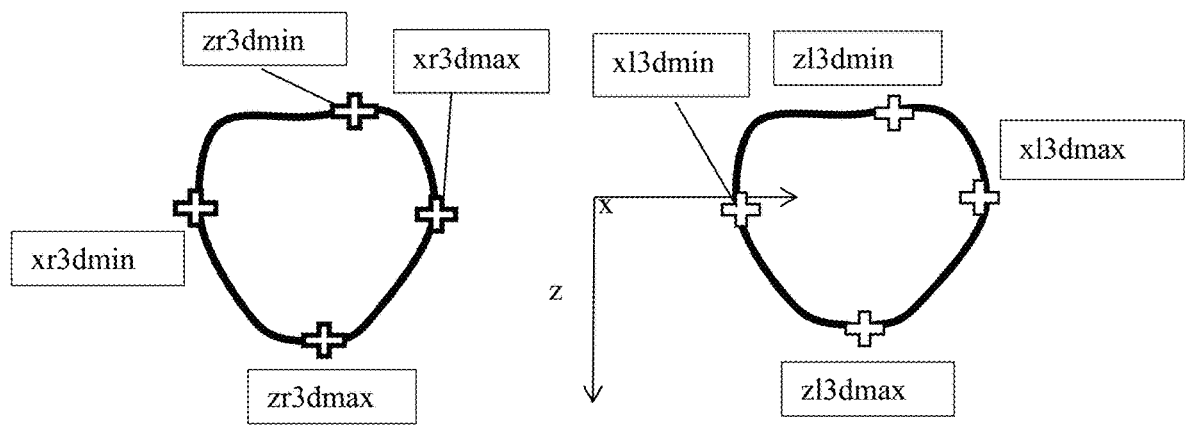
FIGS. 17A and 17B shows an exemplary 4-point template (i.e., two 4-point templates) of a test 3D body shape profile (Left leg/Right leg). This template is used to collect {CP} and {TP} point sets for the 3D body limbs (left/right legs, left/right arms).
Figure 17B:
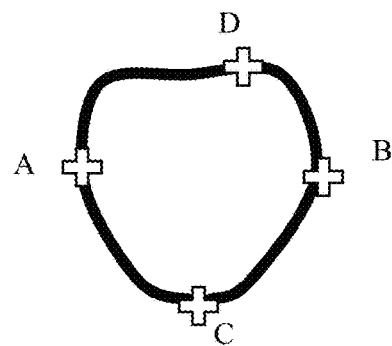
Figure 18:
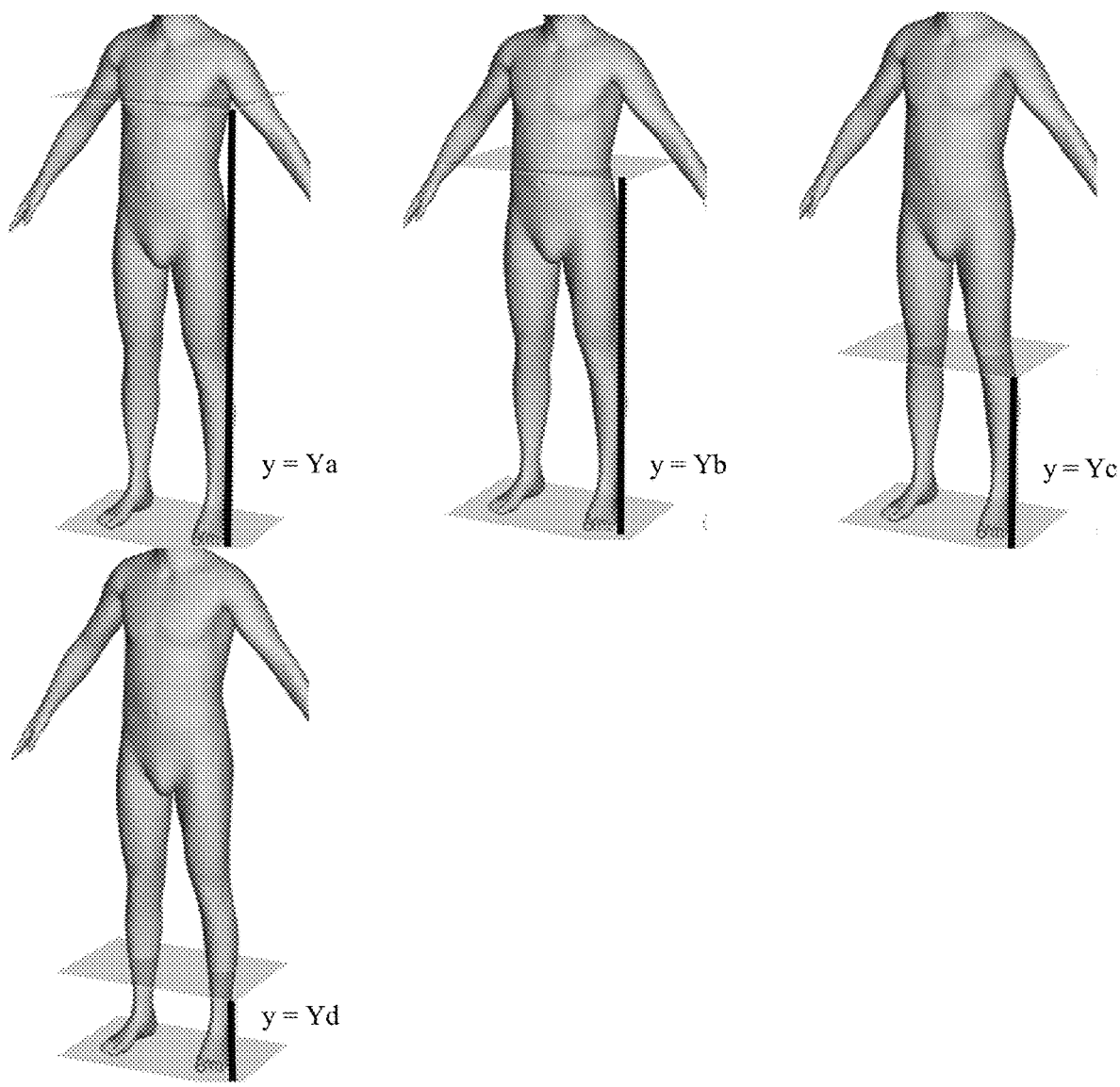
FIG. 18 shows a collection of the control points on the test 3D body based on planes or cross-sections made along various cutting planes of the body. The cutting planes are made parallel to the floor with a constant increment moving up or down the test 3D body. A template, as shown in FIG. 16 or 17, is used to extract 3D points per each cutting plane level.

According to the generic shape of the test body, 2 cross section profile templates can be used, as shown in FIGS. 16-18. A first profile is used for the torso and a second profile is used for the legs and arms of the 3D body.

Each position of the plane, y=Yi, adds a set of 4-6 3D points according to the profile templates (i.e., 6-point templates or 4-point templates may be used). Moving the plane with incremental steps y=y+Yh, and collecting x,y,z coordinates of such points according to the profile templates, the method creates a collection of control points, {CP}.

Next, each point from {CP} is processed to correspond to a topologically equivalent point of the target body with reconstructed x,y,z coordinates of such point in 3D, leading to the collection of target points, {TP}.

The boundary point image coordinates, as shown in FIG. 15, are correlated to projections of the target body points and projections of the cutting planes used for computation of {CP} to the images, with the aim being to reconstruct their coordinates in 3D.

Figure 19:
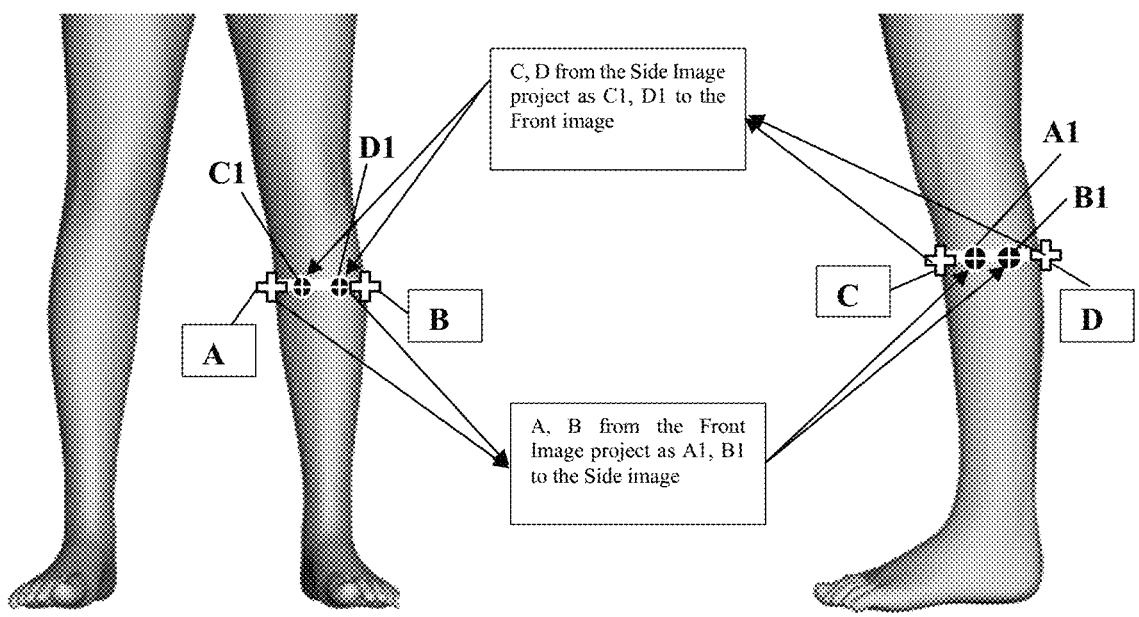
FIG. 19 shows the collecting of image coordinates of target points around a user's leg. Each cutting plane position from FIG. 18 is virtually projected onto the front and side images of the target user's body using the function RF~. Further, mutual image positions of the boundary points are computed based on the projected lines from the front and side images and reconstructed into 3D using function RF. These functions are described and exemplified below. The figure is not drawn to scale, as the cross-sections should be along the same height relative to the test body.

The algorithm starts by creating a virtual projection of the each cutting plane on the test 3D body to the camera sensor planes using a Projection Function (a.7, a.8), where the camera is positioned with known (i.e., already computed) CF and CS coordinates and camera orientation matrices AF, AS. Using function RF~, the method computes vf(Yi) and vs(Yi), which are the image v-coordinates for the front and side images, which define the cutting line (i.e., projection of the cutting plane) in these images as 2D coordinates. This cutting line defines the projection of the 3D cutting plane, y=Yi, into the front and side images obtained for the target body. Each cutting line defines boundary points, as shown in FIG. 15, and therefore image coordinates of these points can be determined. See, e.g., FIGS. 15 and 19. FIG. 15 shows global positions of the boundary points related to a family of cross-section in 3D, correlated to the test 3D body. FIG. 19 shows those boundary points related to just one cross-section from the family of cross-sections shown in FIG. 15, and correlated to a line in 2D for both images. The main point to take away is that image coordinates of the boundary points from both images are obtained for each cross-section in 3D, and therefore all cross-sectional related information may be retrieved in this way, going from one cross-section to the next.

Thereafter, for each boundary point (for example, based on points A and B in the case of the 4-point template) from the front image level vf(Yi), correspondent points, A1 and B1, can be determined on the segment [C, D] of the vs(Yi) level. In the related segment [C, D] with a corresponding level of vs(Yi) from the side image, for each boundary point, C and D, of the level vs(Yi), correspondent points C1 and D1 on the segment [A, B] with a vf(Yi) level from the front image can also be determined. In order to locate point image coordinates, A1, B1 and C1, D1, a test 3D body and a related profile template (See FIG. 16, FIG. 17) are used to compute a linear combination of the boundary points for estimating image points A1, B1 and C1, D1. See FIG. 19.

Example of determination of the point, C1:

"C1" is defined as a linear combination of the boundary points A and B using a linear relation taken from a 3D test body:

$$C1 = A + (z13d\max.x - x13d\min.x)/(x13d\max.x - x13d\min.x) * (B - A);$$

This is similar for D1, A1, and B1.

The reconstruction function, RF, is used to compute 3D coordinates of all boundary points A, B, C, and D, representing and correlating to the given points in a 4-point profile template used for the legs and arms of a user.

$$A(x,y,z) = RF(A(u,v), A1(u,v), CF, CS, AF, AS)$$

B(x,y,z)=RF (B(u,v), B1 (u,v), CF, CS, AF, AS)
C(x,y,z)=RF (C1(u, v), C(u,v), CF, CS, AF, AS)
D(x,y,z)=RF (D1(u,v), D(u,v), CF, CS, AF, AS)

Figure 20:
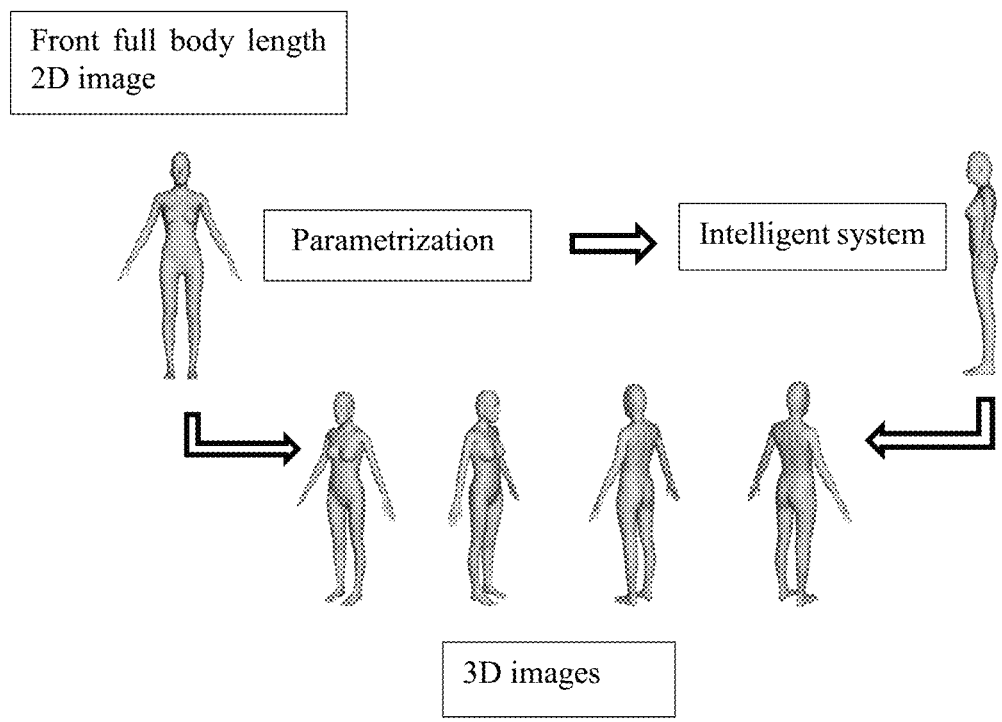
FIG. 20 is a flowchart demonstrating a general exemplary algorithm for methods requiring one image of the user only, the one image being obtained from a 2D camera full body frontal image, which is combined with a simulated intelligent computer system profile (i.e. side) image, the simulated profile image being generated from the full body frontal image, the combination resulting in a 3D body model of the subject's body, which is formed by combining a plurality of segmented 2D images formed from the actual frontal and simulated profile images of the user and same 3D reconstruction method as for both frontal and profile actual 2D images.

It is further noted that for the right leg's points the virtual side camera position should be moved to the left (CS1), with related modification to side camera position CS (CS1=CS(−x,y,z)). And for the 6-point based profile template, for the torso, both side virtual camera positions: left and right, are used An additional disclosed method includes a scanning workflow which requires only one full body length frontal 2D image of the subject. This method is based on substitution of the previously required second 2D profile image of the subject by an image produced by an intelligent computer system which simulates a profile/side image of the subject. This method further simplifies the scan process for the users because the subject no longer needs to provide a second captured image (see FIG. 20).

Figure 26:
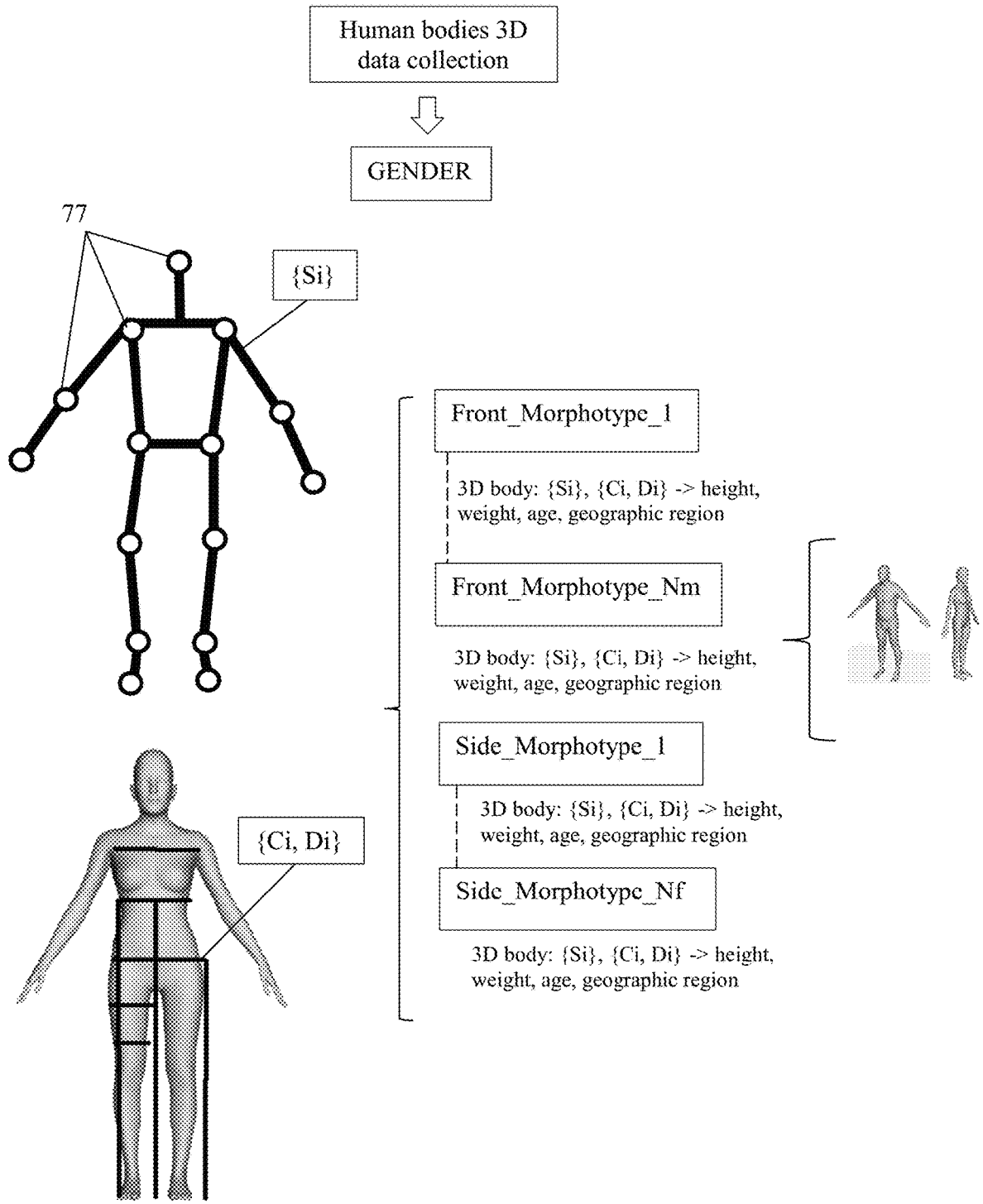
FIG. 26 shows a flowchart of the intelligent computer system and the most probable body match process based on the 3D ($\{Si\}$) parametrization and/or the 2D ($\{Ci, Di\}$) parametrization.

The methods of the present invention allow for the collection of human 3D body models, for example, The collection is then segmented into further classes based on human gender, height, weight, age, demographic data, and morphotypes, with different morphotype definitions for front views and side views (see FIG. 26).

Figure 23:
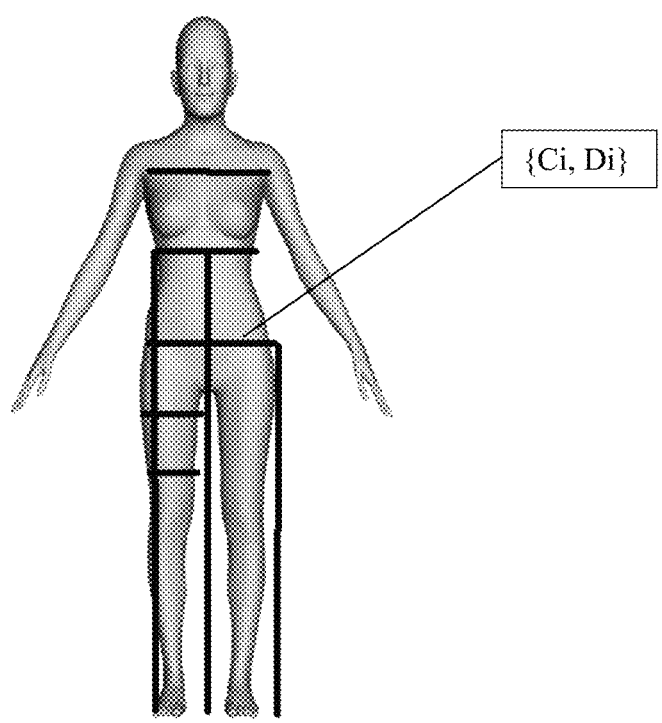
FIG. 23 shows an example of the {Ci, Di} parametrization of a 2D body model, as described hereinbelow.

Parametrization of each 3D body is computed by obtaining the {Si} dimensions of a skeleton, and the {Ci, Di} dimensions per set of horizontal planes (see FIG. 18), where Ci corresponds to body width and Di corresponds to a plane having a known distance from the floor (see FIG. 23).

One or more intelligent systems are then trained to find the most probable body match from known or stored classifications based on the user's input of the subject height, weight, age, geographic region, and set(s) of {Ci, Di} and/or the set of {Si}.

Figure 21:
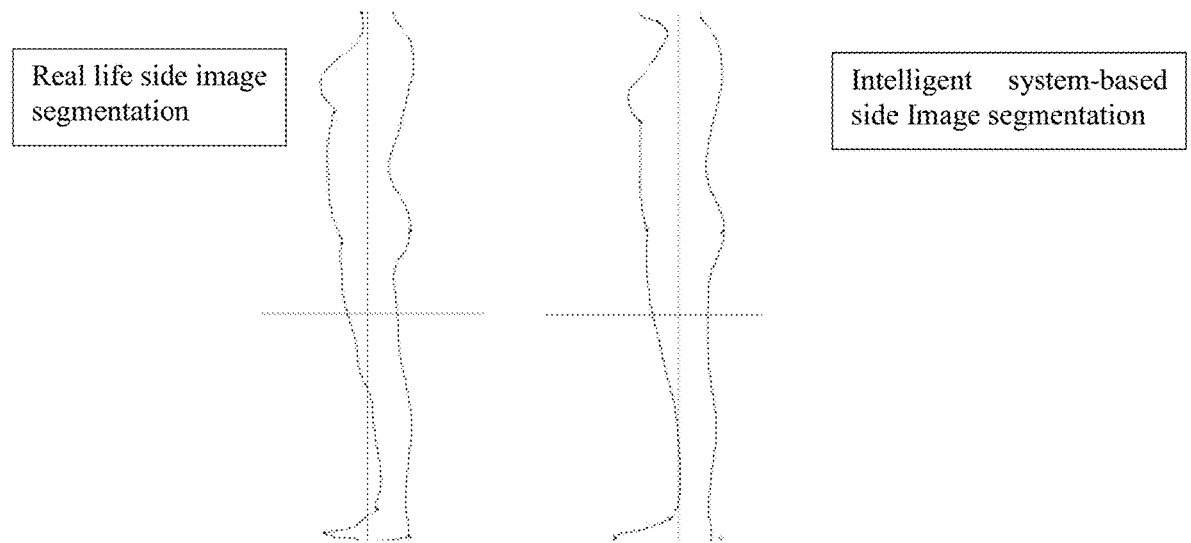
FIG. 21 shows an example of a user side image segmentation comparing a real 2D profile image of the user (left) and a simulated 2D profile image of the user (right).
Figure 22:
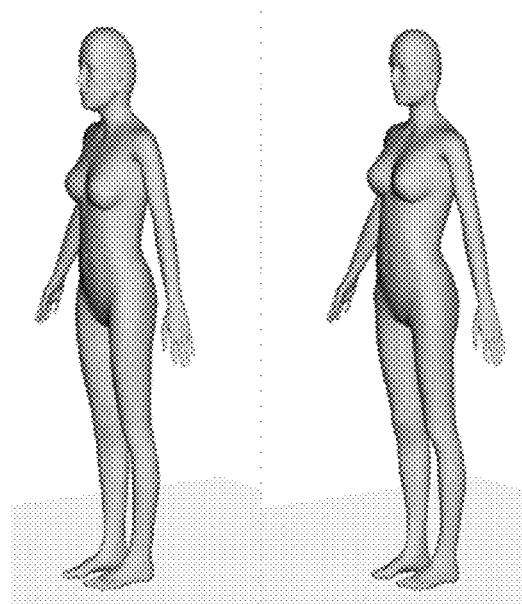
FIG. 22 shows examples of user 3D images created by the invention comparing a 3D image created using a real 2D profile image of a user (left) and a 3D image created using a simulated 2D profile image of a user (right).

After the camera calibration steps as previously described, and after computing the actual camera position in the world coordinate system, the system computes {Si, Di} parametrization of the segmented 2D images (FIG. 23) in 2D image coordinates. The system further reconstructs the {Si, Di} measurement values in 3D using the known camera position, 3D coordinates of the extremity points, and the rule that all {Si, Di} parameters in world coordinates are applied in the plane Z=0. The intelligent computer system is then able to predict a best probable match 3D body based on user-defined height, weight, age, and geographic region, as well as the set(s) of {Ci, Di} parameters computed, if any. The best probable match 3D body is then scaled to the user's height. Thereafter, the 3D body is projected back to the simulated camera to obtain a simulated body profile silhouette of the user (see FIG. 21).

Figure 27:
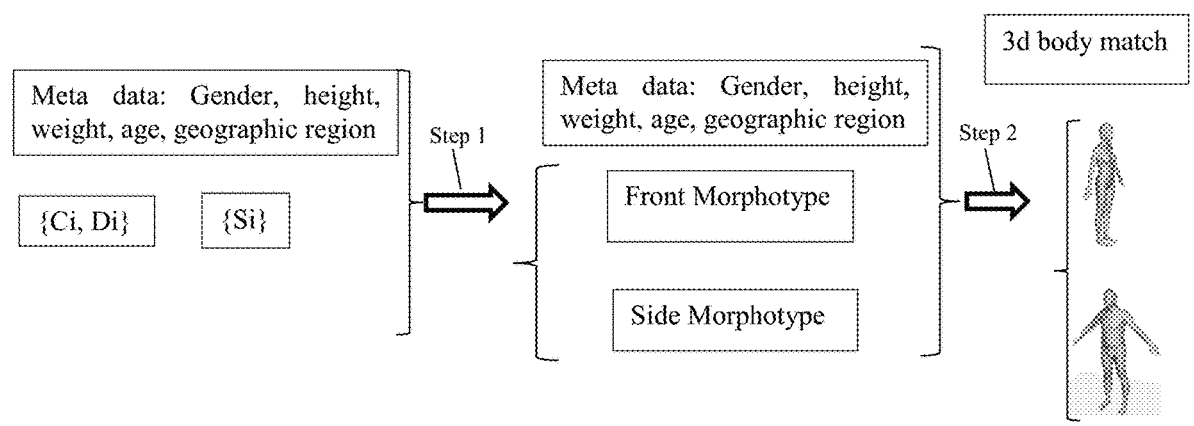
FIG. 27 shows a flowchart of the 2-step intelligent computer system for determining a 3D body most probable match.

An intelligent computer system is trained to work as the user's body morphotype prediction, using original/stored data sets from the Human Bodies Collection. The body morphotype prediction is further segmented by additional morphotype features, such that each body in the collection gets the following key={Gender, Morphotype Front, Morphotype Side, height, weight, age, geographic region, {Si, Di}, {Si}} (see FIG. 26). This intelligent computer system predicts the best probable match 3D body to the user's body, and it works in two steps:

Step 1: Target body Morphotype Prediction. The system uses the subject's metadata as height, weight, age, geographical region, and the target body parametric set, {Si, Di}, computed as described above, to predict, with highest possible probability morphotype of the subject (FIG. 27).

Step 2: Search within the given morphotype segment of the original data set of the Human Bodies 3D Data Collection for the best matching body based on the user's height, weight, age, and geographic location (FIG. 27).

Constructing the Mapping Function, Fm, and Training Fm on {CP} to {TP} Mapping. The mapping function, Fm={Fmx, Fmy, Fmz}, is constructed as a linear combination of the known free form deformation shape function:

$$Fmk(P)=pik*xi(P,Pi), k=x,y,z,$$

where $\chi i$ is a free form deformation shape function (example: radial shape function), Pi is a point from the set {CP}, and βik are unknown coefficients. Using the known mapping between sets {CP} and {TP}, as discussed above, coefficients βik can be found. Training can be performed based on commonly known principals (goals) such as but not limited to collocation and least square.

Training goal example: Fmk (Pj)=Qjk, where Qj={Qjx, Qjy, Qjz}, corresponding to points from set {TP} related to the topologically equivalent point Pj from the set {CP}.

Another example of the training goal:

$$\Sigma(Fmk(Pj)-Qjk)^2 \to \min, k=x,y,z.$$

Both training goal examples lead to the system of linear equation defining coefficients βik.

After Fm is obtained, it is applied on all points of the test 3D body polygon mesh to transform it to a new polygon mesh—which allows for an explicit presentation of the target user's 3D body.

Figure 24:
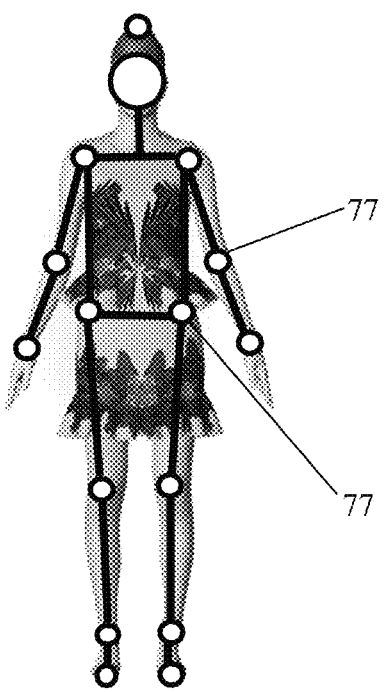
FIG. 24 shows an example of the skeleton joint points ({Si}) 3D parametrization of a subject 2D image using image processing comprising an intelligent computer system, as described hereinbelow.
Figure 25:
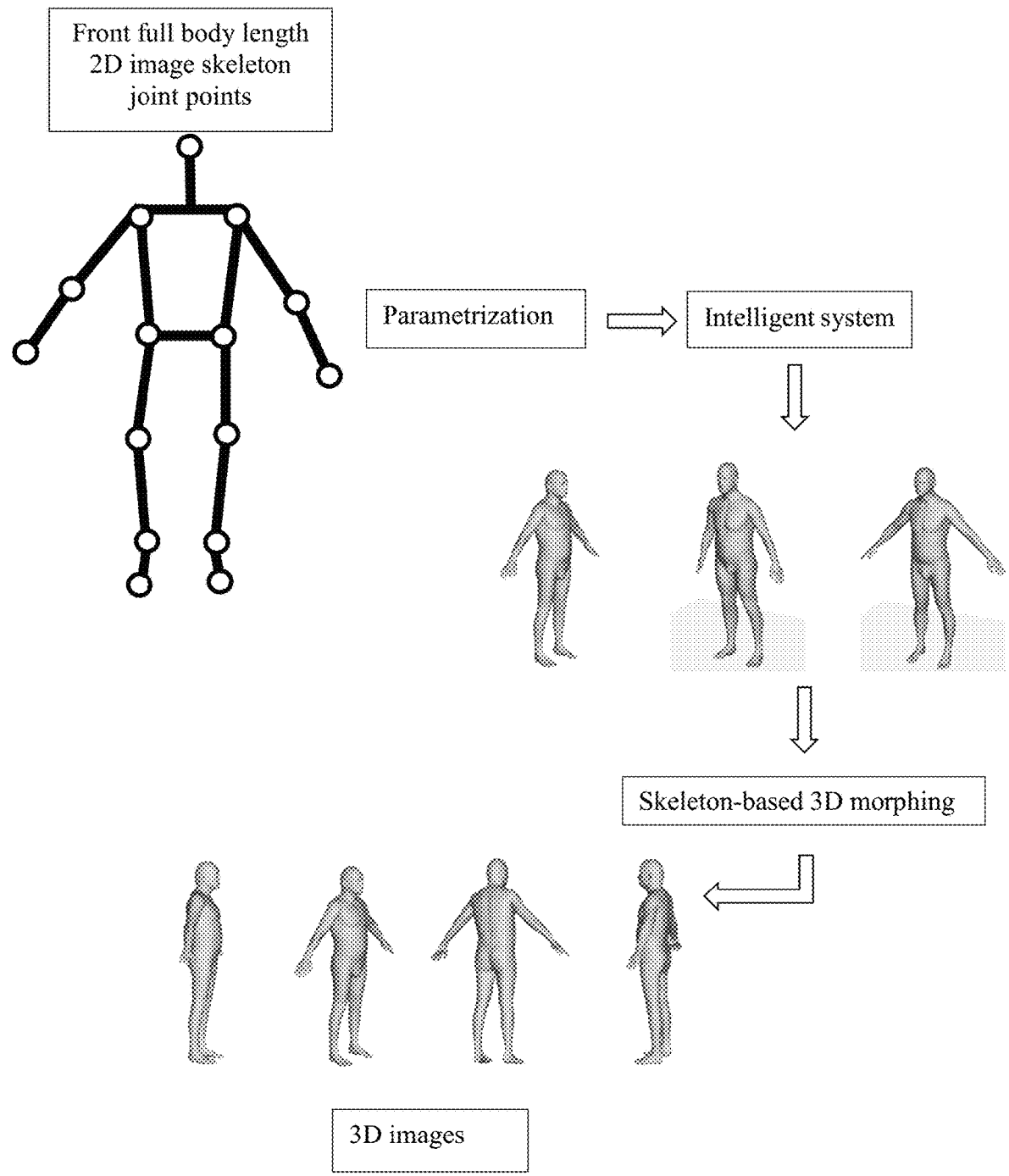
FIG. 25 shows a flowchart of a 3D body most probable match process using the intelligent computer system based on the skeleton joint points ($\{Si\}$) (3D body parametrization).

The intelligent computer system described above can be trained only using {Si} parametrisation, if {Ci, Di} parameters are not available, within the desired accuracy based on current standards. This may be the case, e.g., if the user is wearing casual (non form-fitting) clothing. In this case, the method follows the process as shown in FIG. 25: (1) Extract body skeleton, {Si}, using the captured frontal image (FIG. 24); (2) use an image processing intelligent computer system and run a 3D body match using another intelligent computer system, as described in FIG. 27 and previously in the Specification; (3) The obtained best match 3D body is transformed further using a second mapping function, $F_{m2}$, trained on the {CP}→{TP} sets, where {CP} is based on the {Si} extracted from the frontal 2D image (see FIG. 23), and {TP} is based on the {Si} derived from the obtained best match 3D body.

The description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

Moreover, the words "example" or "exemplary" are used herein to mean serving as an example, instance, or illustration. Any aspect or design described herein as "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

What is claimed is:

1. A method for creating one or more three-dimensional (3D) images of a user, comprising:
   applying form-fitting clothing onto the user,
   positioning a two-dimensional (2D) camera on a planar surface,
   positioning the user facing a lens of the 2D camera,
   via the 2D camera and a processing software:
     capturing a full body length frontal 2D image of the user,
     segmenting the captured fully body length frontal 2D image, thus forming a plurality of segmented 2D frontal images,
     determining extremity points of a user's body in image coordinates, based on the plurality of segmented frontal 2D images,
     determining boundary points of the user's body in image coordinates, based on the plurality of segmented frontal 2D images and the extremity points of the user's body in image coordinates,
     determining a camera sensor position in world coordinates based on camera sensor parameters, camera accelerometer data, and the extremity points of the user's body in image coordinates,
     determining extremity points of the user's body in world coordinates, based on the extremity points of the user's body in image coordinates, and
     determining boundary points of the user's body in world coordinates, based on the boundary points of the user's body in image coordinates,
   via one or more intelligent computer systems and an inputted user height and weight:
     constructing a virtual 3D body model of the user in profile view, the virtual 3D body model having characteristics which match the user's body, and
     projecting the 3D body model of the user in profile view onto the previously determined camera sensor position in world coordinates, thus forming a simulated 2D profile image corresponding to the user,
   via the processing software,
     segmenting the simulated 2D profile image corresponding to the user, thus forming a plurality of segmented 2D profile images,
     determining extremity points of the user for the simulated 2D profile image in image coordinates,
     determining boundary points of the user for the simulated 2D profile image in image coordinates, and
     constructing a 3D model of the user based on said pluralities of segmented 2D frontal and profile images, said constructing a 3D model of the user comprising:
       combining all of said extremity points and boundary points to form a set of computed 3D coordinates, said computed 3D coordinates being target points corresponding to the user's body,
       choosing a test model relatable to the user's body, said test model comprising a set of template points,
       correlating said set of template points to match with said target points of the user's body, thereby forming a set of paired control points, said set of paired control points being fitted into linear combinations of one or more free form deformation functions, and
       mapping a polygon mesh of said test model to obtain a polygon user model, said polygon mesh being formed by fitting the set of paired control points to the target points of the user's body,
     said polygon user model being formed based on said formed polygon mesh and on said linear combinations of one or more free form deformation functions.

2. The method of claim 1, wherein the camera is held by a third party.

3. The method of claim 1, wherein the step of finding a match of the body of the user to a stored 3D body template model is further based on skeleton metrical data determined from the world coordinates.

4. A method for creating one or more three-dimensional (3D) images of a user, comprising:
   applying non form-fitting clothing to the user,
   positioning a two-dimensional (2D) camera on a planar surface,
   positioning the user facing a lens of the 2D camera,
   via the 2D camera and processing software,
     capturing a full body length 2D frontal image of the user,
   via one or more first intelligent computer systems:
     determining extremity points and human skeleton joint points of a user's body using the captured 2D frontal image in image coordinates,
     determining a position of a sensor of the 2D camera in world coordinates,
     determining extremity points and skeleton joints points of the user in world coordinates by correlating image coordinates to world coordinates,
   via one or more second intelligent computer system:
     finding a match of the user's body, said match of the user's body corresponding to one of a plurality of stored 3D body template models, said match being based on data input by the user, and
     using the matching 3D body template model, collecting known extremity points and human skeleton joint points of the 3D body template model, thus forming control points,
     using the user's extremity points and human skeleton joint points in world coordinates, transforming the control points to correlate to target points of the user's body, thus forming a user 3D body model.

5. The method of claim 4, wherein the camera is held by a third party.

6. The method of claim 4, wherein the step of finding a match of the body of the user to a stored 3D body template model is further based on skeleton metrical data determined from the world coordinates.

* * * * *